(12) United States Patent
Viertiö-Oja

(10) Patent No.: US 6,801,803 B2
(45) Date of Patent: Oct. 5, 2004

(54) METHOD AND APPARATUS FOR DETERMINING THE CEREBRAL STATE OF A PATIENT WITH FAST RESPONSE

(75) Inventor: Hanna Elina Viertiö-Oja, Espoo (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 10/123,056

(22) Filed: Apr. 15, 2002

(65) Prior Publication Data

US 2003/0055355 A1 Mar. 20, 2003

Related U.S. Application Data

(63) Continuation-in-part of application No. 09/688,891, filed on Oct. 16, 2000, now Pat. No. 6,731,975.

(51) Int. Cl.[7] .................................................. A61B 5/04
(52) U.S. Cl. ....................... 600/544; 600/545; 600/546; 600/300; 600/301
(58) Field of Search .............................. 600/544–546, 600/300–301, 508

(56) References Cited

U.S. PATENT DOCUMENTS

| | | | |
|---|---|---|---|
| 4,417,590 A | | 11/1983 | Smith et al. |
| 4,421,122 A | | 12/1983 | Duffy |
| 4,705,049 A | | 11/1987 | John |
| 4,753,246 A | * | 6/1988 | Freeman ..................... 600/544 |
| 4,907,597 A | | 3/1990 | Chamoun |
| 5,010,891 A | | 4/1991 | Chamoun |
| 5,109,862 A | * | 5/1992 | Kelen et al. ................. 600/515 |

(List continued on next page.)

FOREIGN PATENT DOCUMENTS

| | | | | |
|---|---|---|---|---|
| GB | 2113846 | | 8/1983 | |
| GB | 2113846 A | * | 8/1983 | ............ A61B/5/00 |
| WO | 91/13584 | | 9/1991 | |

OTHER PUBLICATIONS

Rezek et al., "Stochastic Complexity Measures for Physiological Signal Analysis", IEEE Transaction on Biomedical Engineering, vol. 45, No. 9, Sep. 1998, pp. 1186–1191.*

(List continued on next page.)

Primary Examiner—Robert L. Nasser
Assistant Examiner—Patricia C. Mallari
(74) Attorney, Agent, or Firm—Andrus, Sceales, Starke & Sawall, LLP

(57) ABSTRACT

A method and apparatus for ascertaining the depth of anesthesia of the patient. In one embodiment, the entropy of the patient's EEG signal data is determined as an indication of the depth of anesthesia. A frequency domain power spectrum quantity is obtained from the patient's EMG signal data. The latter quantity can be updated more frequently than the EEG entropy due to its higher frequency. The EEG entropy indication and the EMG power spectrum indication can be combined into a composite indicator that provides an immediate indication of changes in the state of the patient. In a further embodiment, the frequency range over which the entropy of the biopotential signal from the patient is determined is selected to encompass both EEG signal data and EMG signal data and the entropy so determined used as an indication of the patients state. In addition, entropy of the EEG range alone can be used together with the entropy of the broadened range to indicate separately contributions from EEG and EMG. In a more generalized version of the further embodiment, a set of frequency components obtained from selected frequency ranges is utilized in determining entropy. The patient signal data from which the frequency components are extracted are obtained from time windows of differing lengths so that the resulting entropy indication will have optimally fast response times.

40 Claims, 17 Drawing Sheets

U.S. PATENT DOCUMENTS

| | | | |
|---|---|---|---|
| 5,320,109 A | | 6/1994 | Chamoun et al. |
| 5,339,826 A | * | 8/1994 | Schmidt et al. ............. 600/544 |
| 5,458,117 A | | 10/1995 | Chamoun et al. |
| 5,474,082 A | * | 12/1995 | Junker ......................... 600/545 |
| 5,566,678 A | * | 10/1996 | Cadwell ..................... 600/544 |
| 5,579,774 A | | 12/1996 | Miller et al. |
| 5,769,793 A | | 6/1998 | Pincus et al. |
| 5,816,247 A | | 10/1998 | Maynard |
| 5,840,040 A | * | 11/1998 | Altschuler et al. .......... 600/545 |
| 5,846,208 A | * | 12/1998 | Pichlmayr et al. .......... 600/544 |
| 5,857,978 A | | 1/1999 | Hively et al. |
| 6,067,467 A | * | 5/2000 | John ........................... 600/544 |

OTHER PUBLICATIONS

*Electroencephalogram Approximate Entropy Correctly Classifies the Occurrence of Burst Suppression Pattern as Increasing Anesthetic Drug Effect*, Jörgen Bruhn, M.D. et al., Anesthesiology, vol. 93, No. 4, Oct. 2000, pp. 981–985.

New Method to Determine Depth of Anesthesia from EEG Measurements, Poster Presentation and Talk in the Annual Meeting of the Society for Technology in Anesthesia 2000, Jan. 12–15, 2000, Lake Buena Vista, FL.

*Theoretical Electroencephalogram Stationary Spectrum for a White–noise–driven Cortex: Evidence for a General Anesthetic–induced Phase Transition*, Moira I. Steyn–Ross and D.A. Steyn–Ross et al. 1999 The American Physical Society, Physical Review E, vol. 60, No. 6, Dec. 1999, pp. 7299–7310.

*New Method to Determine Depth of Anesthesia from EEG Measurements*, Dr. Hanna Viertio–Oja et al., Journal of clinical Monitoring and Computing, vol. 16, No. 1., Jan. 2000, p. 60.

*Onset of Propofol–induced Burst Suppression May Be Corrected Detected as Deepening of Anaesthesia by Approximate Entropy, But Not by Bispectral Index*, Br. J. Anaesth. 2001 Sep.; 87(3):505–7 by Bruhn Jr., Bouillon, T.W., Shafer, S.L..

*Development Equations for the EEF*, E.R. John, H. Ahn, L. Prichep, T. Trepetin, D. Brown, and H. Kaye, Science, 10980, 210: 1255–1258.

*Entropy of the EEG Signal is a Robust Index for Depth of Hypnosis*, Dr. Hanna Viertio–Oja et al., 2000 SAS Meeting Abstracts, American Society for Anesthesiologists, Oct. 14, 2000, pp. 1–2.

*On the Structure of EEG Development*, A. Alvarez, P.A. Valdes, R.D. Pascual, L. Galan, R. Biscay, and J. Bosch, Electroenceph. Clin. Neurophysiol., 1989, 73: 10–19.

*Quantification of EEG Irregularity by Use of the Entropy of the Power Spectrum*, T. Inouye, K. Shinosaki, H. Sakamotor, S. Toi, S. Ukai, A. Iyama, Y. Katsuda and M. Hirano, Electroencephalography and Clinical Neurophysiology, 70 (1191) 204–210.

*Psychological and Psychopysiological States*, M. Dongier, W.C. McCallum, G. Torres, and W. Vogel, in: A. Redmond (Ed.), Handbook of Electroenceph. Clin. Neurophysiol., vol. 6A, Elsevier, Amsterdam, 1976: 195–254.

*Event–related EEG/MEG Synchronization and Desynchronization: Basic Principles*, Clinical Neurophysiology 110 (1999) pp. 1842–1857.

Bispectral Index (BIX) and Burst Suppression; Reveal a Part of the BIS Algorithm, Bruhn et al., Journal of Clinical Monitoring and Computing, 16: 593–596, 2000.

*Electroencephalographic Indices Related to Hypnosis and Amnesia During Propofol Anaesthesia for Cardioversion*, G. W. Baker et al., Anaesthesia and Intensive Care, vol. 28, No. 4, Aug. 2000, pp. 386–391.

*A Primer for EEG Signal Processing in Anesthesia*, Ira J. Rampil, M.S., M.D., Anesthesiology, vol. 89, No. 4, Oct. 1998, pp. 980–1002.

*Increasing isoflurane concentration may cause paradoxical increases in the EEG bispectral index in surgical patients*, O. Detsch et al., British Journal of Anaesthesia 2000, pp. 33–37.

*Stochastic Complexity Measures for Physiological Signal Analysis*, I. A. Rezek et al., 1998 IEEE Transactions on Biomedical Engineering, vol. 45, No. 9, Sep. 1998, pp. 1186–1191.

*On the Complexity of Finite Sequences*, Abraham Lempel et al., IEEE Transactions on Information Theory, vol. IT–22, No. 1, Jan. 1976, pp. 75–81.

*Approximate Entropy as an Electroencephalographic Measure of Anesthetic Drug Effect during Desflurane Anesthesia*, Jorgen Bruhn, M.D. et al., Anesthesiology, vol. 92 No. 3, Mar. 2000, pp. 715–726.

*A Regularity Statistic for Medical Data Analysis*, Steven M. Pincus, PhD et al., Journal of Clinical Monitoring, vol. 7, No. 4, Oct. 1991, pp. 335–345.

*Predicting Movement during Anaesthesia by Complexity Analysis of Electroencephalograms*, X.S. Zhang et al., Medical & Biological Engineering & Computing, vol. 37, 1999, pp. 327–334.

* cited by examiner

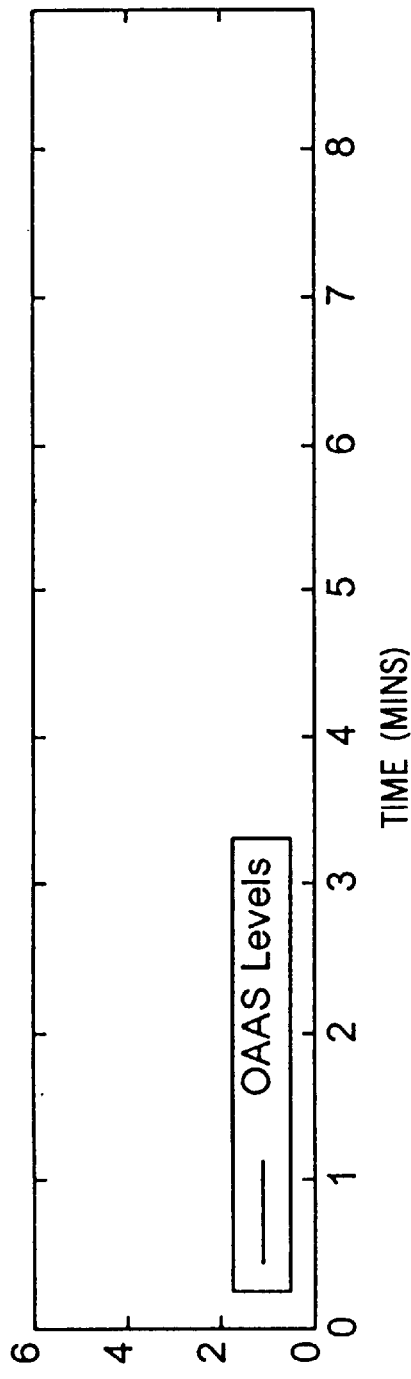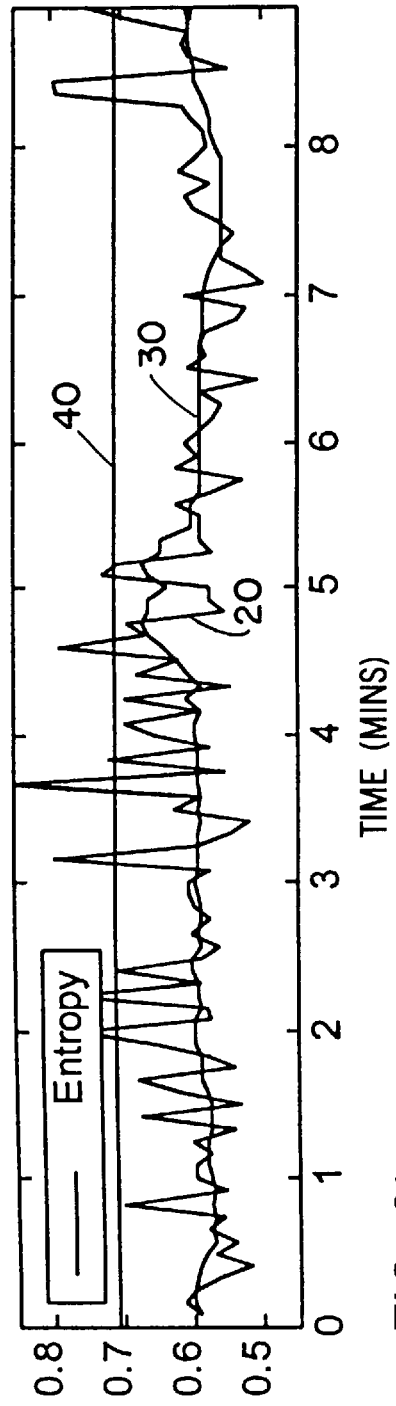
FIG. 3a
FIG. 3b

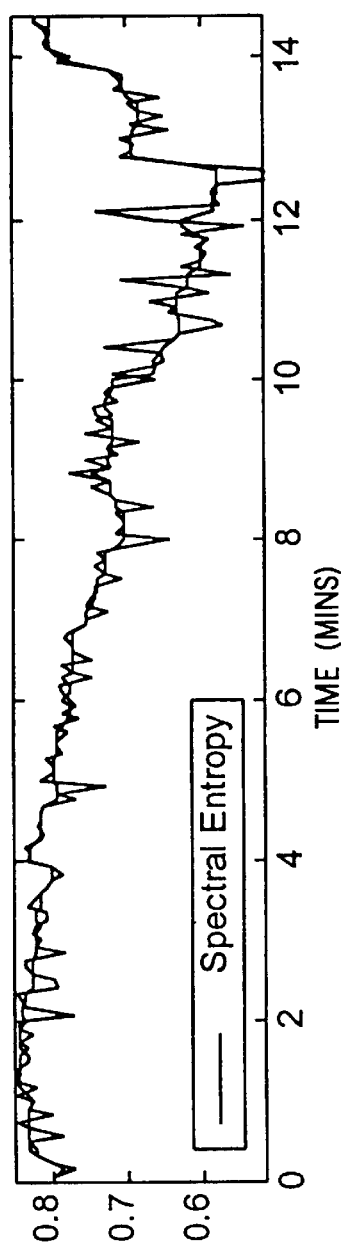
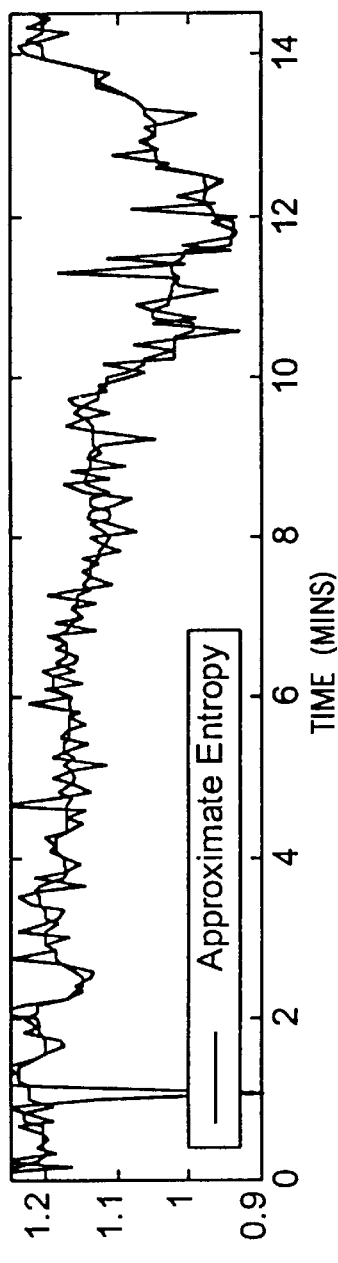
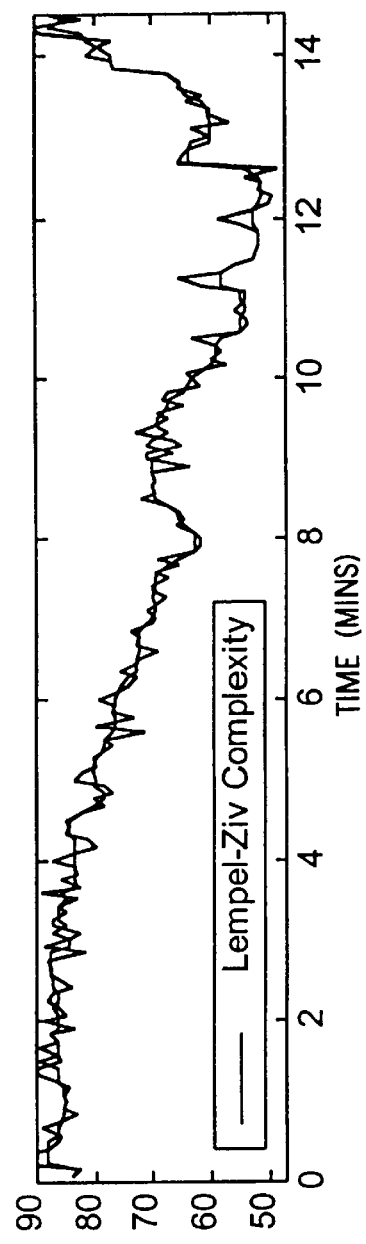
FIG. 5a
FIG. 5b
FIG. 5c

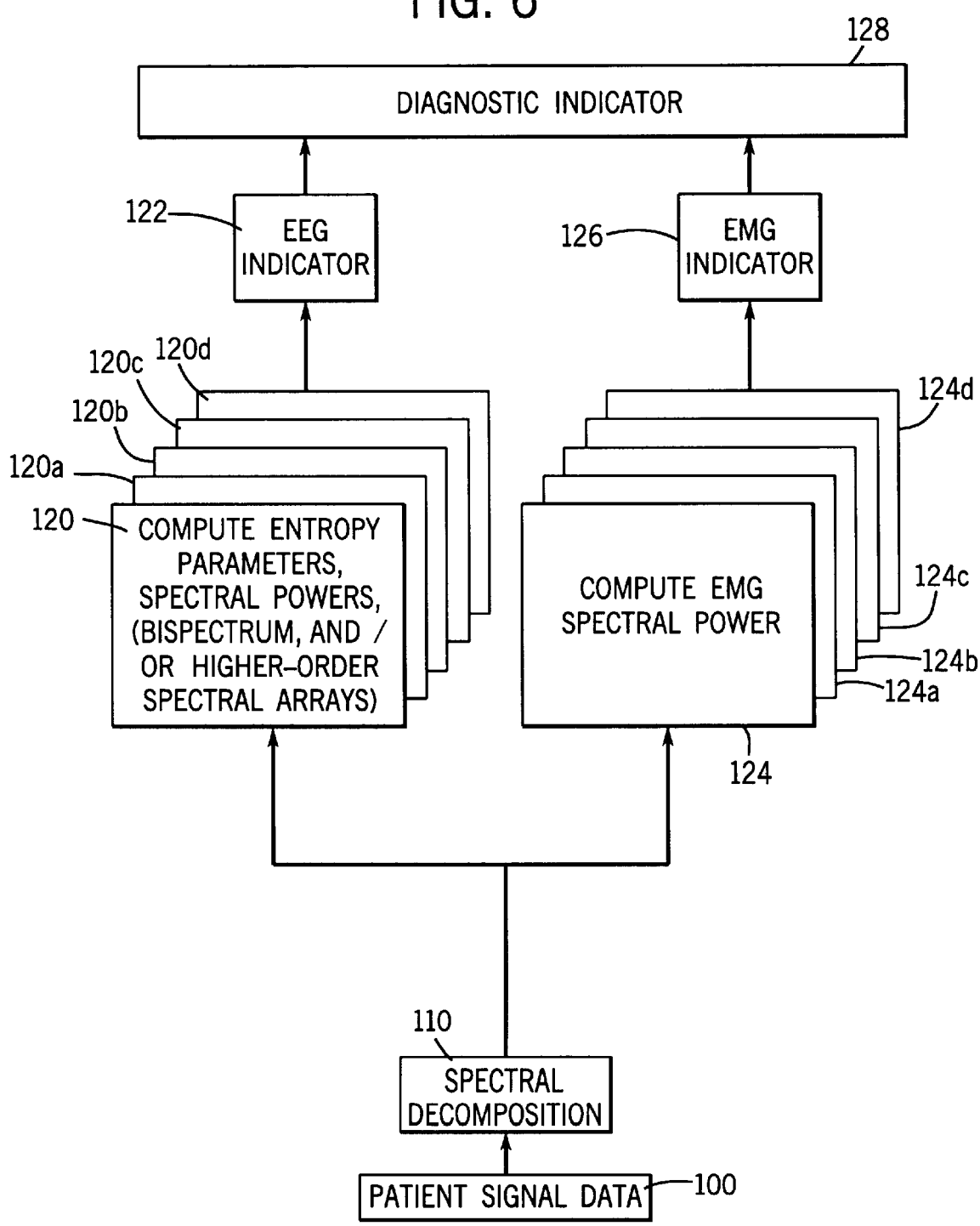

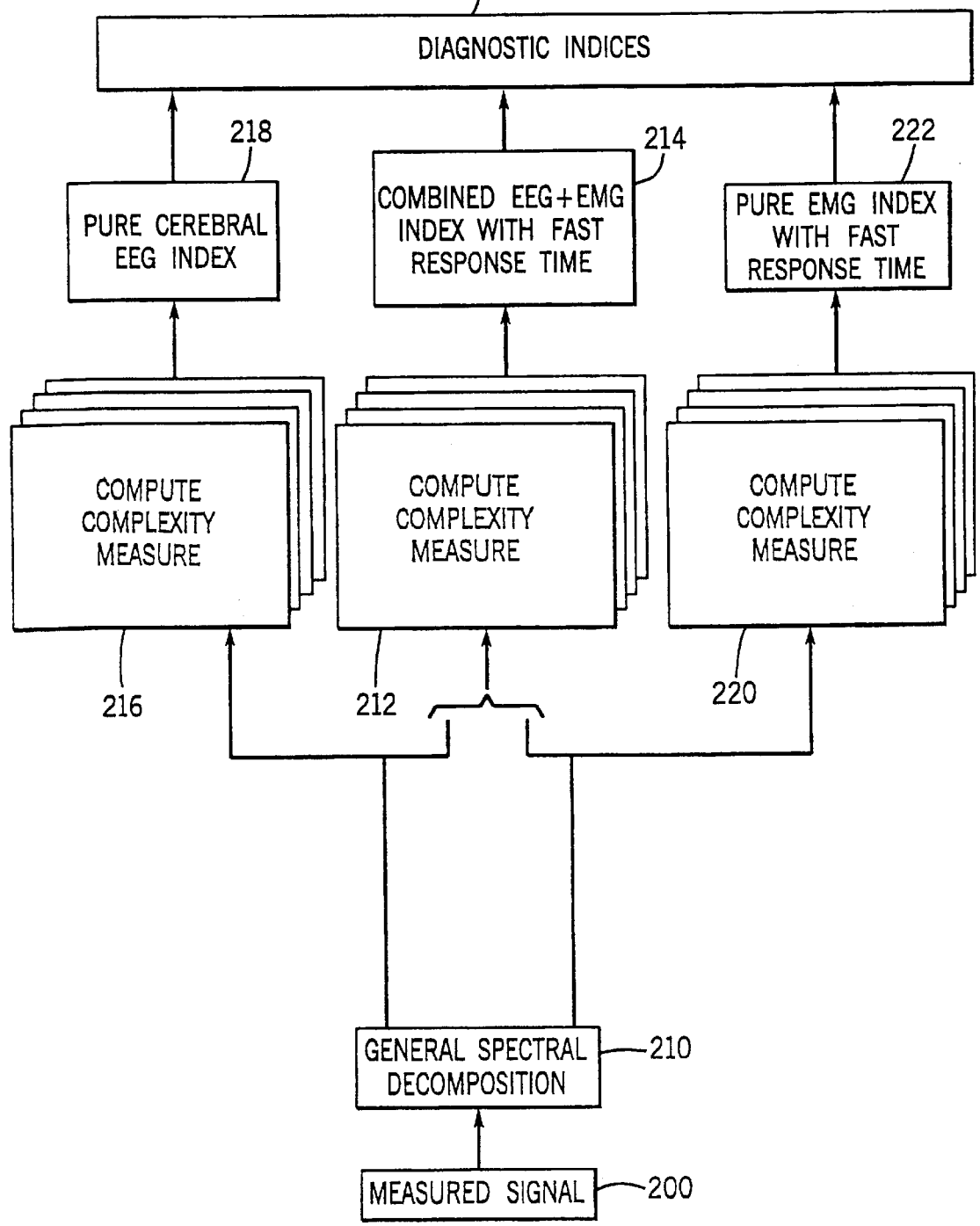

METHOD AND APPARATUS FOR DETERMINING THE CEREBRAL STATE OF A PATIENT WITH FAST RESPONSE

CROSS REFERENCE TO RELATED APPLICATION

The present application is a continuation-in-part application of U.S. patent application Ser. No. 09/688,891, filed Oct. 16, 2000 and now U.S. Pat. No. 6,731,975.

BACKGROUND OF THE INVENTION

The present invention relates to a method and apparatus for determining the cerebral state of a patient. One application of the method and apparatus is determining the extent of a hypnotic state of the patient resulting, for example, from the administration of an anesthetic agent. That extent is often termed the "depth of anesthesia." In the method and apparatus of the present invention, changes in the cerebral state can be accurately and quickly determined.

In a simplistic definition, anesthesia is an artificially induced state of partial or total loss of sensation or pain, i.e. analgesia. For most medical procedures the loss of sensation is accompanied by a loss of consciousness on the part of a patient so that the patient is amnestic and is not aware of the procedure.

The "depth of anesthesia" generally describes the extent to which consciousness is lost following administration of an anesthetic agent. As the magnitude of anesthetization, or depth of anesthesia, increases, an anesthetized patient typically fails to successively respond to spoken commands, loses the eyelid reflex, loses other reflexes, undergoes depression of vital signs, and the like.

While loss of consciousness (hypnosis) and the loss of sensation (analgesia) are significant features of anesthesia, it should be noted that balanced high quality anesthesia must also consider muscle relaxation, suppression of the autonomous nervous system, and blockade of the neuro muscular junction. Sufficient muscle relaxation is required to ensure optimal operating conditions for the surgeon manipulating the patient's tissue. The autonomous nervous system, if not suppressed, causes the patient to respond to surgical activity with a shock reaction that effects heavily on hemodynamics and the endocrine system. To keep the patient motionless, the neuro muscular junctions transmitting orders from the brain to the muscles of the body may be blocked so that the body of the patient becomes paralyzed.

While the need to determine the state of all five components of anesthesia is widely recognized, ascertaining and quantifying the state of hypnosis or depth of anesthesia in a reliable, accurate, and quick manner has been, and is, the subject of extensive attention. One reason for this is its importance. If the anesthesia is not sufficiently deep, the patient may maintain or gain consciousness during a surgery, or other medical procedure, resulting in an extremely traumatic experience for the patient, anesthesiologist, and surgeon. On the other hand, excessively deep anesthesia reflects an unnecessary consumption of anesthetic agents, most of which are expensive. Anesthesia that is too deep requires increased medical supervision during the surgery recovery process and prolongs the period required for the patient to become completely free of the effects of the anesthetic agent. A second reason for the continuing study and attention being given to monitoring the hypnotic condition of a patient arises because of its difficulty: that is, anesthetic agents alter the activity and state of the patient's brain and these changes are not always easy to detect.

A measure of the depth of anesthesia that may be used for research purposes is found in an Observer's Assessment of Alertness and Sedation or OAAS. The OAAS determines the level of consciousness or, conversely, the depth of sedation or anesthesia, based on a patient's response to external stimuli. One such assessment that classifies the depth of anesthesia in six levels, is summarized by the table below. The transition from consciousness to unconsciousness may be deemed to occur when the OAAS score changes from level 3 to level 2. Level zero corresponds to a state of deep anesthesia in which the patient shows no response to a very painful stimulus.

| OAAS Score | Distinctive Characteristics |
| --- | --- |
| 5 | Patient replies readily to spoken commands, eyes open, awake. |
| 4 | Patient is sedated, but replies to spoken commands, mild ptosis. |
| 3 | Patient ceases to reply to loud commands, eye lid reflect present. |
| 2 | Patient does not reply to spoken commands, no eye lid reflex. |
| 1 | Patient does not react to TOF stimulation (50 mA) with movement. |
| 0 | Patient does not react to tetanic stimulation with movement. |

"Ptosis" is a drooping of the upper eyelids. "TOF stimulation" ("train-of-four") is a very short, painful electrical (50 mA) stimulus applied to the ulnar nerve in the arm of the patient, repeated four times to evaluate the intensity of muscular contraction. In "tetanic stimulation" the electrical current (50 mA) is applied continuously for a period of time, such as 5 seconds. The ulnar nerve is the nerve which, when pinched, gives rise to the well known "crazy or funny bone" effect.

While useful for research purposes, an OAAS scale provides only a limited number of scaling levels and is limited in practical use because of the attention required from the anesthesiologist and the use of painful stimuli.

It has long been known that the neurological activity of the brain is reflected in biopotentials available on the surface of the brain and on the scalp. Thus, efforts to quantify the extent of anesthesia induced hypnosis have turned to a study of these biopotentials. The biopotential electrical signals are usually obtained by a pair, or plurality of pairs, of electrodes placed on the patient's scalp at locations designated by a recognized protocol and a set, or a plurality of sets or channels, of electrical signals are obtained from the electrodes. These signals are amplified and filtered. The recorded signals comprise an electroencephalogram or EEG.

Among the purposes of filtering is to remove electromyographic (EMG) signals from the EEG signal. EMG signals result from muscle activity of the patient and will appear in electroencephalographic electrodes applied to the forehead or scalp of the patient. They are usually considered artifacts with respect to the EEG signals.

A typical EEG is shown in FIG. 1. A macro characteristic of EEG signal patterns is the existence of broadly defined low frequency rhythms or waves occurring in certain frequency bands. Four such bands are traditionally recognized: Delta (0.5–3.5 Hz), Theta (3.5–7.0 Hz), Alpha (7.0–13.0 Hz), and Beta (13.0–32.0 Hz). Alpha waves are found during periods of wakefulness and may disappear entirely during sleep. The higher frequency Beta waves are recorded during periods of intense activation of the central nervous system. The lower frequency Theta and Delta waves reflect drowsiness and periods of deep sleep. Even higher frequency EEG patterns than those described above have been investigated, although measurements are difficult due to very low amplitudes of these high-frequency waves.

By analogy to the depth of sleep, it can be said that an overall slowing down of the EEG takes place as the depth of anesthesia increases, while the magnitude of the signal initially often increases. However, this gross characterization is too imprecise and unreliable to use as an indication of such a critical medical aspect as the extent of hypnosis. The foregoing circumstance has led to the investigation and use of other techniques to study EEG waveforms to ascertain the underlying condition of the brain, including the depth of anesthesia to which a patient is subjected. It will be immediately appreciated from FIG. 1 that EEG signals are highly random in nature. Unlike other biopotential signals, such as those of an electrocardiogram (ECG), an EEG normally has no obvious repetitive patterns, the morphology and timing of which can be conveniently compared and analyzed. Nor does the shape of the EEG waveform correlate well to specific underlying events in the brain. Hence, except for certain phenomena, such as epileptic seizures, which are readily apparent from visual inspection of an EEG, the indication of other conditions in the brain in the EEG is much more subtle.

Prefatory to the use of other techniques, the EEG signals are subjected to analog to digital signal conversion by sequentially sampling the magnitude of the analog EEG signals and converting same to a series of digital data values. The sampling is typically carried out at a rate of 100 Hz or greater. The digital signals are stored in the magnetic or other storage medium of a computer and then subjected to further processing to ascertain the underlying state of the brain. Such processing typically uses sets of sequential EEG signal samples or data points representing a finite block of time, commonly termed an "epoch." The analysis of the data is usually carried out on a moving average basis employing a given epoch and a certain number of backward epochs.

Some of the techniques by which EEG signals can be analyzed in an effort to determine the depth of anesthesia are well described in Ira J. Rampil, *A Primer for EEG Signal Processing in Anesthesia*, Vol. 89, Anesthesiology No. 4, pgs. 980 et seq., October 1998.

One such technique is to examine, in some meaningful way, how the voltage of an EEG signal changes over time. Such an analysis is termed a "time-domain analysis." However, an EEG signal is not a deterministic signal This means that it is not possible to exactly predict future values of the EEG from past values in the manner that, for example, the shapes of past QRS complexes in an ECG signal can be used to predict future values for analytical and diagnostic purposes. Rather, it is a stochastic signal for which certain statistical characteristics of the signal can be predicted.

Time-domain based analysis is useful in the study and quantification of burst suppression in the EEG. During deep anesthesia, the EEG time-domain signal may develop a pattern of activity which is characterized by alternating periods or "bursts" of normal, or high frequency and amplitude, voltage signals and periods of low or no voltage, which periods are termed those of "suppression." The extent of this phenomenon can be expressed as a "burst suppression ratio (BSR)" which is a time domain EEG parameter describing the time the EEG voltage is in the suppressed state as a fraction of the sampling period.

A second approach to analyzing EEG waveforms examines signal activity as a function of frequency, i.e. a "frequency-domain analysis." It has long been recognized that complex waveforms, such as EEG signals, can be decomposed, or transformed, into a plurality, or spectrum, of simple sine or cosine waves of various frequencies, amplitudes, and phases. Frequency-domain spectra can be obtained from sequential time-domain EEG signal data by a Fourier transform. Frequency-domain analysis analyzes the spectrum of frequency signals obtained from the transform to determine characteristics and features occurring in wave forms having the various frequencies of the spectrum. The components of the resulting Fourier transformation corresponding to any particular frequency are complex numbers which can be characterized by an amplitude and a phase value. The amplitude information is typically graphically displayed as a power versus frequency histogram in which frequency is graphed on the abscissa and power, which corresponds to the amplitude squared, is graphed on the ordinate.

Further efforts to obtain useful information from electroencephalograms have employed higher order analyses, including the bispectrum and trispectrum. The bispectrum, which measures the correlation of phase between two different frequency components and quantifies the relationships among the underlying sinusoidal components of the EEG, has received considerable attention. The bispectrum specifically quantifies the relationship between sinusoids at two primary frequencies $f_1$ and $f_2$ and a modulation component at the frequency $f_1+f_2$. A strong phase relationship between $f_1$, $f_2$ and $f_1+f_2$ creates a large bispectral value for frequency $f_1+f_2$.

For clinical use, it is desirable to simplify the results of EEG signal analysis of the foregoing, and other types, into a workable parameter that can be used by an anesthesiologist in a clinical setting when attending the patient. Ideally, what is desired is a simple, single parameter or index that quantifies the depth of anesthesia on a consistent, continuous scale extending from full alertness to maximally deep, but reversible, hypnosis. To be fully useful such a scale should maintain its consistency, notwithstanding the differing pharmacological effects of different anesthetic agents, as well as the differing physiologies of different patients.

Various such parameters for relating EEG signal data to the hypnotic state of the patient are discussed in the literature. Several use frequency domain power spectral analysis. These parameters include peak power frequency (PPF), median power frequency (MPF), and spectral edge frequency (SEF). A peak power frequency (PPF) parameter uses the frequency in a spectrum at which occurs the highest power in the sampled data as an indication of the depth of anesthesia. The median power frequency (MPF) parameter, as its name implies, uses the frequency that bisects the spectrum. In the same fashion, the spectral edge frequency uses the highest frequency in the EEG signal. A modification of the latter is the SEF 95 parameter, which is the frequency below which 95% of the power in the spectrum resides.

To improve the consistency of an indicator of the hypnotic state or depth of anesthesia, several parameters may be employed in combination. For example, the spectral edge frequency (SEF) parameter may be combined with the time-domain burst suppression ratio (BSR) parameter to extend its use to the deepest regimen of anesthesia.

While parameters of the foregoing types can detect changes in the EEG caused by anesthetic agents and hence are useful in determining the depth of anesthesia, they suffer from an inability to be calibrated to behavioral endpoints, as well as from sensitivity to the different EEG patterns induced by different anesthetic agents.

More complex combinations of parameters are described in U.S. Pat. Nos. 4,907,597; 5,010,891; 5,320,109; and 5,458,117 to Nassib Chamoun or Chamoun et al. and are employed in the anesthesia monitor product made and sold by the assignee of the patents, Aspect Medical Systems of Framingham, Mass. The patents describe various combinations of a time-domain subparameter and frequency-domain subparameters, including a high order spectral subparameter, to form a single variable that correlates behavioral assessments of sedation and hypnosis over a range of anesthesia for several anesthetic agents. Because of this ability, the Aspect Medical Systems product has found clinical acceptance.

In the form implemented in the product, the parameter, called bispectral index, BIS, consists of the following four subcomponents: SyncFastSlow, BetaRatio, Burst Suppression (BSR), and "QUAZI". The calculation of the subparameter SyncFastSlow utilizes bispectral analysis in the frequency-domain. The SyncFastSlow parameter corresponds to the logarithm of the ratio of the sum of all bispectral peaks in the frequency range 0.5–47 Hz divided by the sum in the range 40–47 Hz. The BetaRatio subparameter gives the logarithm of the power ratio in the frequency ranges 30–47 Hz and 11–20 Hz. It is a frequency-domain parameter that has been found to work best in light sedation. As noted above, in very deep levels of anesthesia, EEG signal contains data samples in which the EEG activity is suppressed. The Burst Suppression Ratio obtained from a time-domain analysis of the EEG signal describes the relative content of burst and suppression in the signal. The Burst Suppression Ratio is operative in deep anesthesia in which the suppression occurs. The parameter "QUAZI" detects burst suppression when it is superimposed on very slow waves, (<1 Hz). See Ira J. Rampil in Anesthesiology, supra.

The resulting bispectral index, BIS, is a combination of these four subparameters. The combining algorithm weights the different subparameters according to their range of best performance. While the details of the algorithm are unpublished and proprietary, it is known that different subparameters or combinations of subparameters are employed depending on the level of hypnosis or depth of anesthesia. BetaRatio predominates in light anesthesia, SynchFastSlow in surgical levels, and BSR and QUAZI at deep levels of anesthesia. The function that determines the weights for these subparameters was originally developed by a statistical procedure by fitting the parameter to a behavioral scale using a large collected database of EEG measured during anesthesia.

While this approach is systematic and scientifically sound, it has inherent limitations. As the technique requires changing from one algorithm to another depending on the level of anesthesia, a question arises whether these changes are made consistently, or whether there are perhaps, problems at the boundaries of the BetaRatio-dominated, SynchFastSlow-dominated, and BSR/QUAZI-dominated regions.

Some recent studies point to the conclusion that such problems exist. In "Onset of propofol-induced burst suppression may be correctly detected as deepening of anaesthesia by approximate entropy but not by bispectral index", Br J Anaesth 2001 September; 87(3):505–7 by Bruhn et al, observations were reported in which BIS failed to show deepening anesthesia at the onset of burst suppression. In a subsequent study, accepted for publication in Journal of Clinical Monitoring and Computing, Bruhn et al. derived the functional dependence of BIS on BSR. Up to 40% suppression ratio, the average BIS values remained constant regardless of suppression ratios Beyond a suppression ratio >=40%, BIS and suppression ratio were invariably linearly correlated, following the equation BIS=50−suppression ratio/2 The results indicated also that there is a range of values between 30 and 40 in which BIS is relatively insensitive to changes in drug concentration. It is plausible that such a region is required in order to switch smoothly from a "SynchFastSlow"-dominated algorithm to a "BSR/QUAZI-dominated" algorithm. The problem may thus be a direct consequence of the way BIS is constructed. Detsch, et al., in "Increasing Isoflurane Concentration may cause Paradoxical Increases in the EEG bispectral index in Surgical Patients", Br. J. Anaesth. 84 (2000), pgs. 33–37 reported paradoxical behavior of BIS at increasing isoflurane concentrations in approximately the same range of BIS values.

It is less clear whether similar problems are found at the higher boundary region of BIS between the "BetaRatio"- and "SynchFastSlow"-dominated ranges. The apparently discontinuous jump of BIS often seen at loss of consciousness may be related to a switching of the algorithm, but it may also be a consequence of a real state transition of the cortex that is reflected in the EEG signal.

Further, computation of the bispectral index (BIS) parameter requires averaging at least 15 seconds of EEG data. Thus, this index may be not sufficiently fast to detect changes in the state of a patient as is required in the clinical situation. See, Baker, et al. *Electroencephalographic Indices Related to Hypnosis and Amnesia During Propofol Anaesthesia for Cardioversion*, Anaesthesia and Intensive Care, Vol. 28, No. 4, 2000. This may cause a practical problem in the use of the BIS index. An anesthesiologist who has a measurement of anesthetic depth available, is likely to more precisely titrate the amount of anesthetic agent administered to a patient, and is thus likely to reduce the amount of agent administered in order to improve the state of the patient after recovery and to reduce costs. However, the lessened amount of anesthetic agent may increase the risk that the patient will awaken during surgery. It is therefore essential that an anesthesiologist knows immediately if a patient starts to approach consciousness out of the hypnotic state.

A different approach to the analysis of electroencephalographic signals is to attempt to quantify the regularity or irregularity of the highly random EEG signal for use as an indication of the depth of anesthesia. It is known that developmental factors such as maturation (John et al, *Development Equations for the EEG*, Science, 210, (1980) pgs. 1255–1258 and Alvarez et al., *On the Structure of EEG Development*, Electroenceph, Clin. Neurophysiol., 1989, 73:10–19) and attention (Dongier et al. *Psychological and Psychophysiological States* in A. Rémond (Ed), Handbook of Electroenceph. Clin. Neurophysiol., Vol. 6A, Elsevier, Amsterdam, 1976: pgs. 195–254) increase the irregularity of the EEG signal. Concentration on a particular mental task has been shown to result in a greater degree of local desynchronization of EEG (Pfurtscheller et al., *Event-related EEG/MEG Synchronization and Desynchronization: Basic Principles*, Clinical Neurophysiology 110 (1999) pgs. 1842–1857, Inoye et al. *Quantification of EEG Irregularity by use of the Entropy of the Power Spectrum*, Electroencephalography and Clinical Neurophysiology, 79 (1991) pgs. 204–210). These findings suggest that an active cortex generally has a more irregular EEG patterns than an inactive cortex.

There are a number of concepts and analytical techniques directed to quantifying the irregularity and complex nature of random or stochastic signals, such as the EEG. One such concept is entropy. Entropy, as a physical concept, is proportional to the logarithm of the number of microstates available to a thermodynamical system, and is thus related to the amount of disorder in the system. When used in information theory and signal analysis, entropy addresses and describes the irregularity, complexity, or unpredictability characteristics of a signal. In a simple example, a signal in which sequential values are alternately of one fixed magnitude and then of another fixed magnitude has an entropy of zero, i.e. the signal is completely regular and totally predictable. A signal in which sequential values are generated by a random number generator has greater complexity and a higher entropy.

Applying the concept of entropy to the brain, the premise is that when the mind is full of activity the state of the brain is more complex. Since EEG signals reflect the underlying state of brain activity, this is reflected in relatively more "irregularity" or "complexity" in the EEG signal data, or, conversely, in a low level of "order." As a person falls asleep or is anesthetized, the brain function begins to lessen and becomes more orderly and regular. As the activity state of the brain changes in such circumstances, it is plausible to consider that this will be reflected in the EEG signals by a relative lowering of the "irregularity" or "complexity" of the EEG signal data, or conversely, increasing "order" in the signal data.

With respect to anesthesia, an increasing body of evidence indeed shows that EEG signal data contains more "order", i.e. less "irregularity", and lower entropy, at higher concentrations of an anesthetic agent, i.e. greater depth of anesthesia, than at lower concentrations. At a lower concentration of anesthetic agent, the EEG signal has higher entropy. This is due, presumably, to lesser levels of brain activity in the former state than in the latter state. See "Stochastic complexity measures for physiological signal analysis" by I. A. Rezek and S. J. Roberts in IEEE Transactions on Biomedical Engineering, Vol. 4, No. 9, September 1998 describing entropy measurement to a cut off frequency of 25 Hz and Bruhn, et al. "Approximate Entropy as an Electroencephalographic Measure of Anesthetic Drug Effect during Desflurane Anesthesia", Anesthesiology, 92 (2000), pgs. 715–726 showing that approximate entropy of the EEG, measured in a frequency range of 0.5 to 32 Hz, closely follows the concentration of the anesthetic drug in the brain See H. Viertiö-Oja et al. "New method to determine depth of anesthesia from EEG measurement" in J. Clin. Monitoring and Comp. Vol. 16 (2000) pg. 16 and H. E. Vierti ö-Oja et al. "Entropy of EEG signal is a robust index for depth of hypnosis", Anesthesiology 93 (2000) A, pg. 1369, which report that entropy behaves monotonously as a function of anesthetic depth evaluated by the OAAS scale and the transition from consciousness to unconsciousness takes place at a universal critical value of entropy which is independent of the patient.

One reason for the usefulness and success of the entropy concept may reside in the fact that it is a scale-invariant measure that is independent of the frequency and amplitude scales of the signal. The absolute frequencies of EEG rhythms are known to vary from patient to patient, and therefore techniques that use measures defined in terms of the absolute frequency scale, such as the spectral edge frequency, discussed above, may suffer from such variation among patients.

The pertinence of the concept of entropy to the conscious and unconscious states of the brain is also supported in recent theoretical work (see Steyn-Ross et al., Phys. Rev. E60 1999, pgs. 7229–7311) which applies thermodynamic theory to the study of the brain. The results of this work suggest that when a patient undergoing anesthetization passes from the conscious state to the unconscious state, a thermodynamic phase transition of the neural system of the brain takes place which is roughly analogous to the phase change occurring when water freezes into ice. During the process of freezing, an amount of thermodynamical entropy, proportional to the latent heat of the process, is removed so that water and ice have different entropies. According to the theory, the conscious and unconscious states of the brain should have distinct, different values of entropy. While thermodynamical entropy is conceptually different from the entropy in information theory, it is plausible to assume a close correlation between the two in this context. In a well-ordered anesthetized state the neurons are obviously likely to have more regular firing patterns that are reflected in a more regular EEG signal than in the more disordered awake state. If this theory is experimentally proven, it will lend further support to the concept of entropy as a fundamental characteristic of the cerebral state of the brain.

In sum, the following can be said. First, certain forms of entropy have generally been found to behave consistently as a function of anesthetic depth. This warrants consideration of entropy as a natural and robust choice to characterize levels of hypnosis. Also, because entropy correlates with depth of anesthesia at all levels of anesthesia, it avoids the need to combine various subparameters as in the bispectral index (BIS). Second, the transition from consciousness to unconsciousness takes place at a critical level of entropy which is independent of the patient. Thirdly, and of particular practical significance, recovery of a patient toward consciousness from anesthesia can often be predicted by a rise of entropy toward the critical level.

A number of techniques and associated algorithms are available for quantifying signal irregularity, including those based on entropy, as described in the Rezek and Roberts article in IEEE Transactions on Biomedical Engineering article, supra. One such algorithm is that which produces spectral entropy for which the entropy values are computed in frequency space. Another algorithm provides approximate entropy which is derived from the Kolmogorov-Sinai entropy formula and computed in Taken's embedding space. See Steven M. Pincus, Igor M. Gladstone, and Richard A. Ehrenkranz, "A regularity statistic for medical data analysis", J. Clin. Monitoring 7 (1991), pgs. 335–345. A program for computing approximate entropy is set out in the Bruhn et al., article in Anesthesiology. The spectral entropy and approximate entropy techniques have found use in analyzing the complexity of EEG signal data.

Another technique for non-linear analysis of highly random signals is expressed in Lempel-Ziv complexity in which the complexity of a string of data points is given by the number of bytes needed to make the shortest possible computer program which is able to generate the string. See Abraham Lempel and Jacob Ziv, "On the complexity of finite sequences", IEEE Trans., IT-22 (1976) pgs. 75–81.

A still further approach that may be applied to EEG signal analysis is fractal spectrum analysis based on chaos theory. In fractal spectrum analysis, the EEG signal is divided into a harmonic component and a fractal component. The harmonic component includes the simple frequencies whereas the fractal component contains the part which is invariant under scaling in time. It has been found that the fractal exponent Beta which corresponds to the frequency power law $1/f^\beta$ increases consistently in the course of deepening anesthesia (Viertiö-Oja et al. J. Clin. Monitoring).

BRIEF SUMMARY OF THE INVENTION

An object of the present invention is to provide an improved method and apparatus for accurately determining the cerebral state of a patient, including the hypnotic or consciousness state of a patient and the depth of anesthesia that a patient is experiencing.

A particular object of the present invention is to provide such a method/apparatus that can rapidly make such determinations, especially when a patient is emerging to the conscious state from unconsciousness.

The gist of the present invention is to combine an effective measure of the cerebral state of a patient derived from EEG signal data, preferably a complexity measurement such as spectral entropy or approximate entropy, with a more rapidly obtainable measure derived from EMG signal data and to use the combination as a state indication. The measure derived from the EMG signal data may comprise spectral power data. When used as an indication of the hypnotic state, or depth of anesthesia, of the patient, the measure derived from the EMG signal data enhances and confirms the determination of the hypnotic state made using the EEG signal data and renders predicting changes in the hypnotic state of the patient more rapid. This is of particular advantage in alerting an attending anesthesiologist to the possibility that an anesthetized patient may shortly regain consciousness so that the anesthesiologist can take timely, appropriate action.

Both the EEG and EMG signal data are typically obtained from the same set of electrodes applied, for example, to the forehead of the patient. The EEG signal component dominates the lower frequencies (up to about 30 Hz) contained in the biopotentials existing in the electrodes. At higher frequencies, EEG power decreases rapidly and exponentially. The EMG signal has a wide noise-like spectrum and dominates at frequencies higher than 30 Hz.

Sudden appearance of EMG signal data often indicates that the patient is responding to some external stimulus, such as a painful stimulus, i.e. nociception, due to some surgical event. Such a response may result if the level of analgesia is insufficient. If stimulation continues and no additional analgetic drugs are administered, it is highly likely that the level of hypnosis eventually starts to lighten. EMG can thus provide a rapid indication of impending arousal. Importantly, because of the higher frequency of the EMG data signal, the sampling time can be significantly shorter than that required for the lower frequency EEG signal data. This allows the EMG data to be computed more frequently so that the overall diagnostic indicator can quickly indicate changes in the state of the patient.

In one embodiment of the invention, the EEG signal data and the EMG signal data are separately analyzed and thereafter combined into a diagnostic index or indicator. As noted above, because of the celerity with which changes in the anesthetic state of the patient can be determined from the EMG data, the overall index can quickly inform the anesthesiologist of changes in the state of the patient.

In a further embodiment of the present invention, the spectral range of the complexity computations, i.e. entropy computations, is widened to extend into the EMG range. Thus, the spectral range over which the complexity computations are carried out to provide an indicator may extend from some lower frequency of, for example 0.5 Hz, up to a frequency above 32 Hz. For example, in an embodiment in which the spectral range extends to approximately 47 Hz, a lower frequency band (0.5–32 Hz) will contain mostly EEG signal data while the upper band (32–47 Hz) will include primarily EMG activity. The use of a widened frequency range does not require a division of the spectrum into two segments as does the first embodiment because all components in the widened frequency range are treated in the same manner.

Further, the complexity measurement obtained in this second embodiment of the invention can be updated as often as is permitted by the higher frequencies of the EMG signal data in the widened spectral range of the complexity computation. This will provide a very current indication to the anesthesiologist of the depth of anesthesia of the patient.

The indicator obtained from the signal complexity computation over the widened spectral range can be used in conjunction with a complexity measurement obtained only from the EEG portions of the frequency spectrum to provide useful information to the anesthesiologist regarding what portion of the indicator comes from cerebral activity and what portion comes from muscle activity.

In a more generalized version of the further embodiment of the invention, a set of frequency components obtained from selected frequency ranges is utilized in determining entropy. The patient data from which the frequency components are extracted are obtained from time windows of differing lengths. For lower frequency components, a longer time window is used. For higher frequency components, a shorter time window is used. By selecting the length of each time window to correspond to a particular frequency range, so that not more than the necessary amount of existing, historical data is used, the resulting complexity measures will have optimally fast response times.

Various other features, objects, and advantages of the invention will be made apparent from the following detailed description and the drawings.

BRIEF DESCRIPTION OF THE SEVERAL VIEWS OF THE DRAWING

FIGS. 3a and 3b are graphs showing values of entropy of a patient at surgical levels of anesthesia;

FIGS. 5a, 5b, and 5c are comparative graphic showings of various techniques for analyzing EEG signals;

FIG. 6 is a flow chart showing one embodiment of the present invention;

FIG. 9 is a flow chart showing another embodiment of the present invention;

DETAILED DESCRIPTION OF THE INVENTION

In a preferred embodiment of the invention, relevant information with respect to depth of anesthesia is extracted from the EEG signal data by computing a parameter that characterizes the amount of disorder or complexity in the signal. Suitable mathematical techniques include, for example, spectral entropy described in Rezek and Roberts, approximate Kolmogorov-Sinai entropy described in Pincus et al., and complexity described in Lempel-Ziv. The use of spectral entropy is deemed advantageous because of its superior computational simplicity. It also has the particular advantage that contributions to entropy from any particular frequency range can be explicitly separated in the analytical expression, as will be discussed below.

Computation of the spectral entropy of a signal according to Rezek and Roberts includes four steps. The first is the power spectrum calculation. The Fourier transform $X(f_i)$ of the signal $x(t_i)$ is computed by the fast Fourier transform technique (FFT). The power spectrum $P(f_i)$ is calculated by squaring the amplitudes of each element $X(f_i)$ of the Fourier transform:

$$P(f_i) = X(f_i) * X^{\wedge}(f_i) \quad (1)$$

where $X^{\wedge}(f_i)$ is the complex conjugate of the Fourier component $X(f_i)$ and '*' denotes multiplication.

The power spectrum is then normalized. The normalized power spectrum $P_n(f_i)$ is computed by setting a normalization constant $C_n$ so that the sum of the normalized power spectrum over the selected frequency region $[f_1,f_2]$ is equal to one:

$$\sum_{f_i=f_1}^{f_2} P_n(f_i) = C_n \sum_{f_i=f_1}^{f_2} P(f_i) = 1 \quad (2)$$

In the summation step, the spectral entropy corresponding to the frequency range $[f_1,f_2]$ is computed as a sum $$S[f_1, f_2] = \sum_{f_i=f_1}^{f_2} P_n(f_i) \log\left(\frac{1}{P_n(f_i)}\right) \quad (3)$$

Thereafter, the entropy value is normalized to range between 1 (maximum irregularity) and 0 (complete regularity). The value is divided by the factor $\log(N[f_1,f_2])$ where $N[f_1,f_2]$ is equal to the total number of frequency components in the range $[f_1,f_2]$:

$$S_N[f_1, f_2] = \frac{S[f_1, f_2]}{\log(N[f_1, f_2])} \quad (4)$$

In the original work by Rezek and Roberts, the frequency range considered was the range below $f_2=25$ Hz, as it is generally assumed that most measurable power of the EEG activity is confined to the frequency band below approximately 32 Hz.

FIG. 2 shows, as a function of time, values of entropy as computed above as compared to an OAAS scale for a patient receiving an anesthetic agent.

Figure 2A:
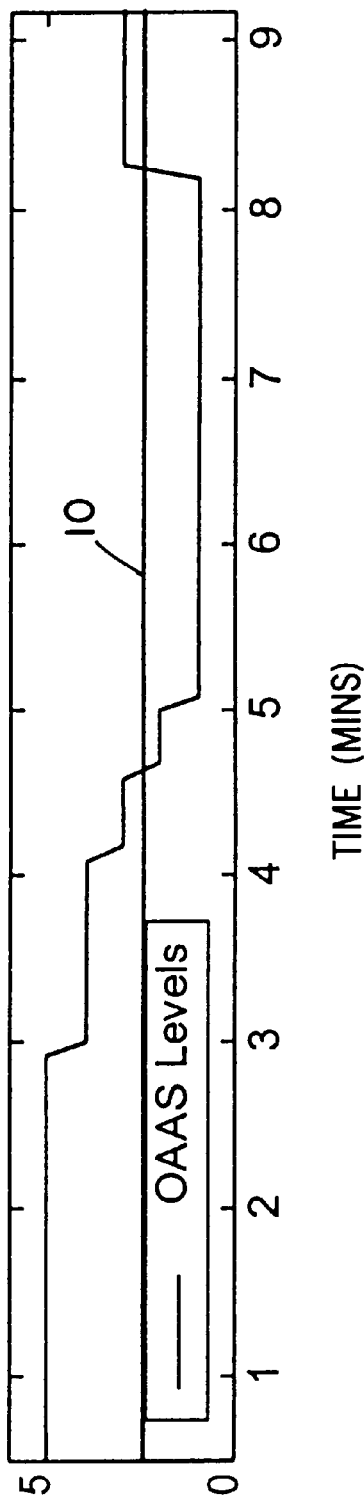
FIGS. 2a and 2b are graphs showing values of entropy as compared to the conventional OAAS scale for a patient receiving an anesthetic agent.

FIG. 2a indicates the OAAS level as determined by an anesthesiologist attending the patient. As noted above, at an OAAS level 5, the patient is fully awake whereas the OAAS level 0 corresponds to a deep state of anesthesia in which the patient shows no response to tetanic stimulation. Horizontal line 10 indicates a level at which transition from the conscious to unconscious state is deemed to take place, i.e. between OAAS level 3 and OAAS level 2.

In the example shown in FIG. 2, the attending anesthesiologist considers the patient to have moved from OAAS level 5 to OAAS level 4 at about three minutes. At about four minutes, the patient is deemed to have dropped to OAAS level 3.

Thereafter, at about four and a half minutes, the patient is deemed to have lost consciousness as by failing to respond to verbal commands and the loss of the eyelid reflex. This is evidenced in the change from level 3 to below level 2 and the crossing of horizontal line 10.

Figure 2B:
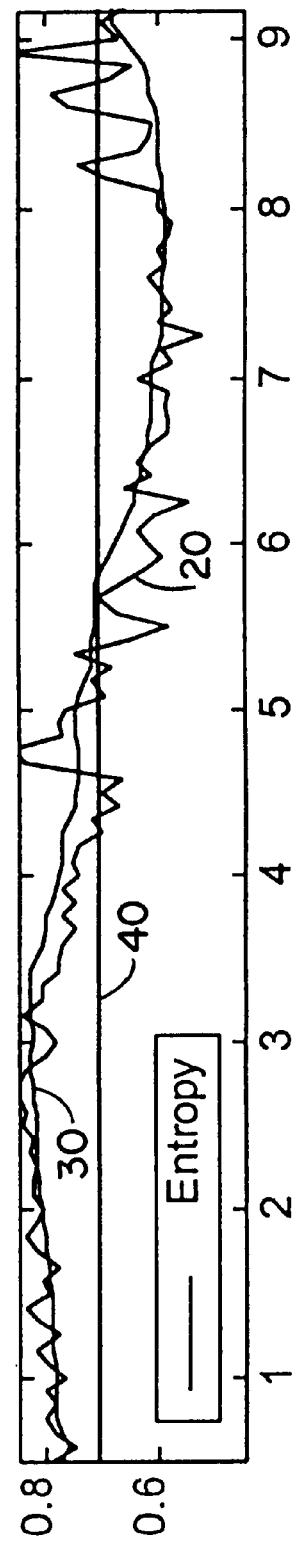

FIG. 2b shows a value of entropy computed from five seconds of data as graph 20 and a value of entropy computed as median values of twelve sequential five second epochs (sixty seconds) of data as graph 30. As can be seen from FIG. 2b, as the consciousness of the patient decreases from the commencing of monitoring, both graphs 20 and 30 similarly decrease and cross horizontal line 40 which identifies the entropy level that characterizes the transition from the conscious state to the unconscious state.

In accordance with a protocol for the OAAS in use, the anesthesiologist commences the application of TOF stimulations to determine the depth of anesthesia on the OAAS scale. In the case shown in FIG. 2, the stimulations cause the patient to regain consciousness at about eight minutes.

It will be seen from FIG. 2 that graphs 20 and 30 follow, and provide an accurate indication of, the state of consciousness of the patient, as presented on the OAAS scale.

Figure 1:
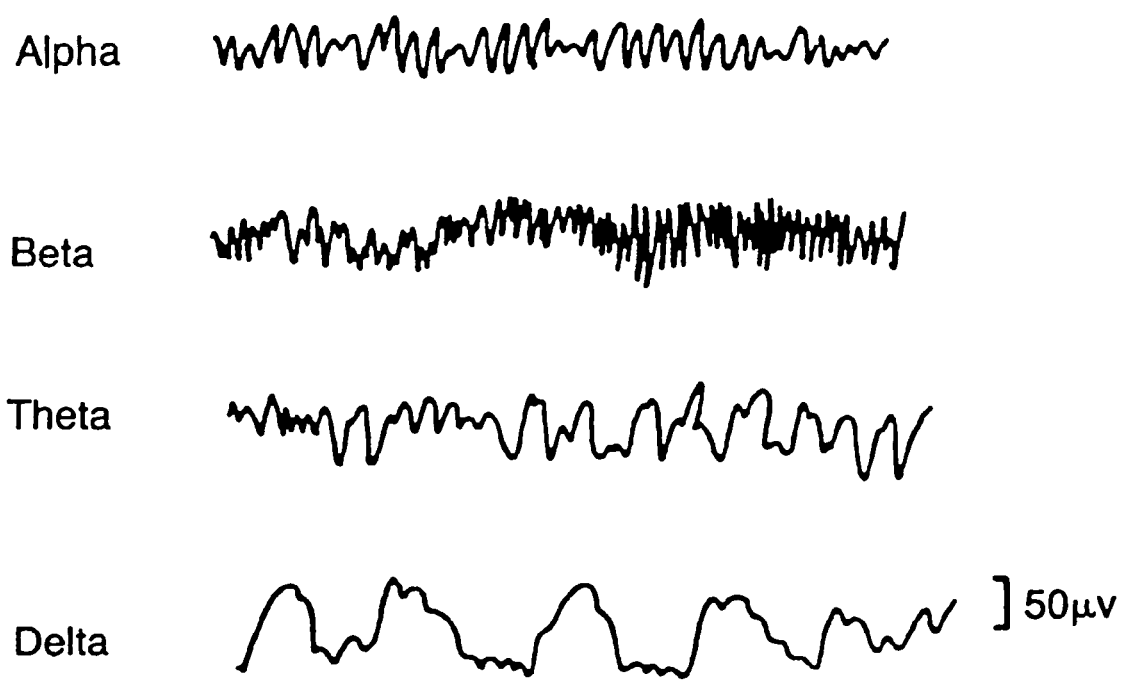
FIG. 1 shows an electroencephalogram.

FIGS. 3a and 3b show the values of entropy at surgical levels of anesthesia, i.e. when the OAAS scale is zero as shown in FIG. 3a. Horizontal line 40 in FIG. 3 is the same as horizontal line 40 in FIG. 1 and comprises the entropic value forming the borderline between the conscious and unconscious states.

Figure 4A:
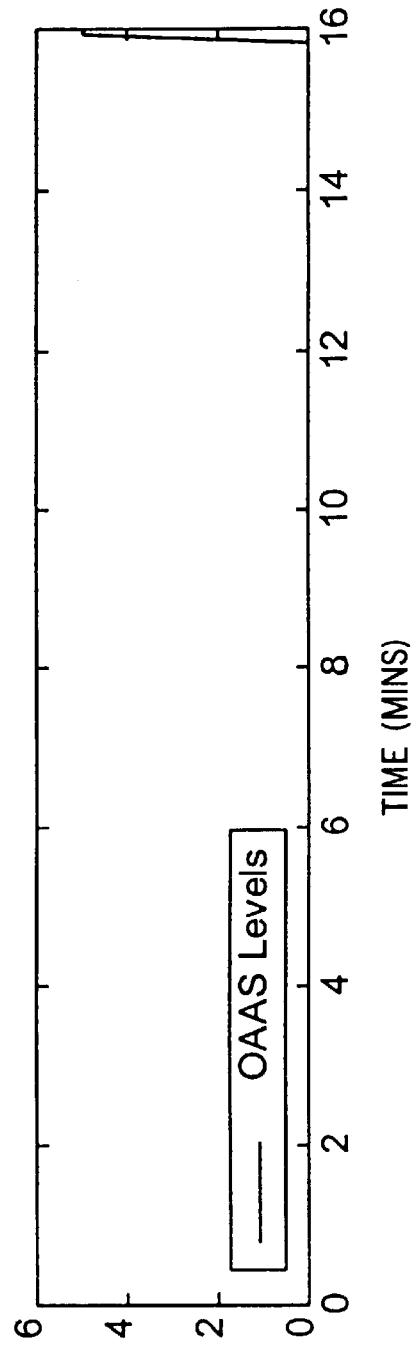
FIGS. 4a and 4b are graphs showing values of entropy as compared to the conventional OAAS scale for a patient emerging from anesthesia.
Figure 4B:
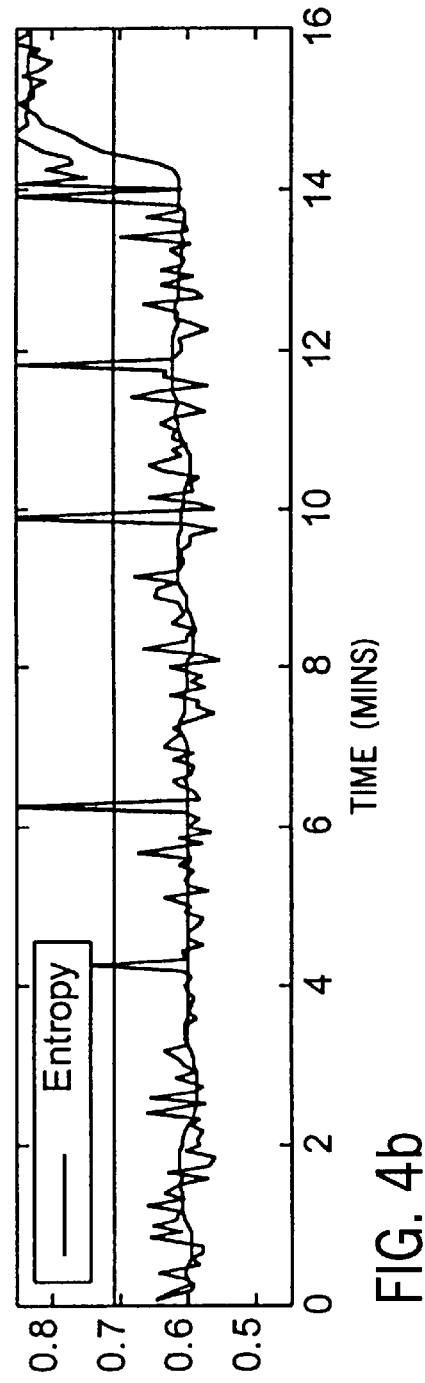

FIGS. 4a and 4b shows a rapid recovery of a patient from surgical levels of anesthesia to consciousness. The rise in the values of entropy, informs the anesthesiologist of the approaching recovery to the conscious state.

While the invention has been described as using spectral entropy, FIGS. 5a, 5b, and 5c illustrate an example of anesthesia induction and emergence showing the suitability of the complexity measurements of approximate entropy and Lempel-Ziv complexity, as well as spectral entropy, to determine the depth of anesthesia. Measurements made using both shorter and longer samples of signal data are shown.

Other techniques for analyzing the EEG signal data can also be used, if desired, such as higher order frequency domain analysis including the bispectrum and trispectrum, frequency domain power spectral analysis, and combinations of analytical quantities, such as the bispectral index (BIS).

Measurement of electromyographic (EMG) activity contained in the biopotentials in the electrodes on the forehead, or other region of the scalp, of the patient can provide useful information concerning the state of an anesthetized patient As the level of anesthesia approaches inadequacy, a painful stimulus causes a contraction of the frontalis muscle (frowning) which can be detected as peaks in the EMG amplitude of the signal obtained from the electrodes applied to the forehead of the patient. EMG responsivity exists as long as the muscles are not paralyzed. This response can often be observed substantially before the pain eventually brings the patient to consciousness.

Further, due to the high frequency range of the primary portion of the EMG activity above 30 Hz, a comparatively small time window is sufficient for computations using these frequency components, so that changes in the EMG activity can be detected substantially faster than changes in the EEG signal. Specifically, most of the component in the EEG signal resulting from brain activity that can be reliably measured in the noisy clinical environment is contained in the frequency range below 30 Hz. In order to obtain a good estimate of this activity by any mathematical procedure, the length of the signal used for computations has to be sufficient. In practice, the lowest frequency of the band sets the size for the signal length. For example, for an EEG signal band from 0.5 Hz to 32 Hz, a signal sample 60 seconds long is required to obtain at least 30 cycles for the slowest 0.5 Hz component. This sets a lower limit to the response time for assessing changes in patient brain activity from the EEG signal data. That is, the frequency with which all components of the EEG signal data indicator can be computed with high precision is about once every 60 seconds. By contrast, an EMG signal data, for example in a 60–90 Hz band, requires only 0.5 seconds of data to obtain 30 cycles. The EMG signal data can thus be fully updated every half second. Because it can be so quickly updated, the EMG signal data can provide an early warning sign for the anesthesiologist to increase, for example, the level of anesthetic agent administered to the patient in order to prevent awareness during surgery.

FIG. 6 is a flow chart showing the steps for producing an improved diagnostic indication using EEG signal data and more rapidly indicative EMG signal data in accordance with one embodiment of the present invention. In step 100, the signal data corresponding to the biopotentials appearing in the electrodes placed on the scalp of the patient is obtained. In step 110, the signal data is subjected to spectral decomposition. This may, for example, be carried out using Fourier analysis.

The spectra are then divided into those representing the low frequency portions of the measured signal, for example, less than 30 Hz and those representing the high frequency portion of the measured signal for example, those representing frequencies of 30 Hz and above.

Thereafter, the EEG spectrum portion is processed at step 120 to compute a parameter indicative of the state of activity of the brain. As noted above, it is presently deemed preferable to use a computation of entropy for this purpose. However, other quantifications such as fractal spectrum analysis, Lempel-Ziv complexity, or bispectral or multispectral analyses, such as the bispectral index (BIS), can be used for this purpose. The result of this computation is the provision of an indication of the state of activity of the brain at step 122.

As noted above, in order to obtain a good estimate of this activity by the mathematical analyses described herein, the length of the signal used for computations has to be sufficient. In practice, the lowest frequency of the band sets the lower limit for the signal length. In the case of the EEG indication generated at step 120, if frequencies as low as 0.5 Hz are included in the analysis, the lower limit for the signal length is approximately 60 seconds. This means the indication can only be completely updated by repeating steps 100, 110, 120, and 122 every 60 seconds and sets a lower limit to the response time of the EEG indication for assessing the patient's cerebral state.

A power spectrum of the EMG signal is obtained in step 124, as by obtaining an amplitude spectrum and thereafter squaring the values of the amplitude spectrum to create a power spectrum. The EMG power spectrum provides an indication of EMG activity in step 126.

Due to the high frequency range of the EMG activity, for example, above 30 Hz, a comparatively small time window, for example 0.5 seconds, is sufficient to compute the EMG amplitude. This means that changes in the EMG activity can be detected and the indicator updated by repeating steps 100, 110, 124, and 126 substantially faster than changes in the EEG indicator, as shown graphically at steps 124, 124a, 124b, etc.

In the example used above, the EMG indicator can be completely updated at a repetition rate of every 0.5 seconds. For simplicity in data processing, the EEG indication will typically also be recomputed every 0.5 seconds. However, since the EEG indicator requires 60 seconds of data, each computation 120, 120a, 120b, etc. will use 59.5 seconds of old EEG signal data and 0.5 seconds of new EEG signal data. Thus, the changes in the cerebral state of the patient contained in the EEG signal data will be reflected more slowly in the indication produced in steps 120 and 122 than the changes contained in the EMG indication.

The EEG indicator and the EMG indicator are combined in a diagnostic indicator or index in step 128.

The indicators produced in steps 120, 122, 124, 126 and 128 may be subjected to statistical treatment, such as averaging, if desired.

The combined indication provided by the diagnostic index of step 128 thus provides both reliable information of the activity state of the brain, such as the level of hypnosis or depth of anesthesia as directly found in the EEG signal data, while full advantage can be taken of the rapidly obtainable information included in the EMG component of the signal, which while not a direct indication of the cerebral state of the patient, is particularly useful in alerting the anesthesiologist to the emergence of a patient from anesthesia.

Figure 7A:
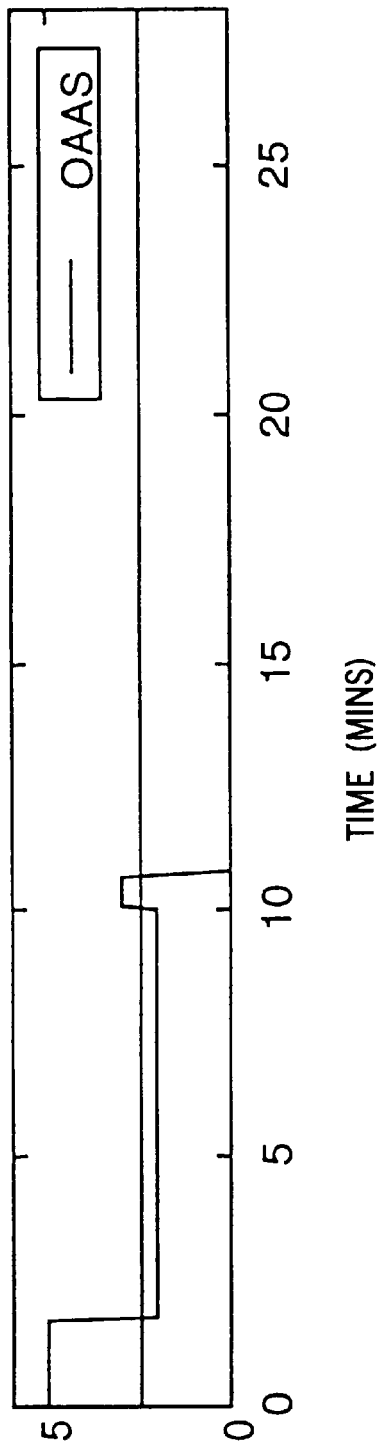
FIGS. 7a, 7b, and 7c are graphs showing OAAS levels, EEG entropy, and EMG amplitude, respectively.
Figure 7B:
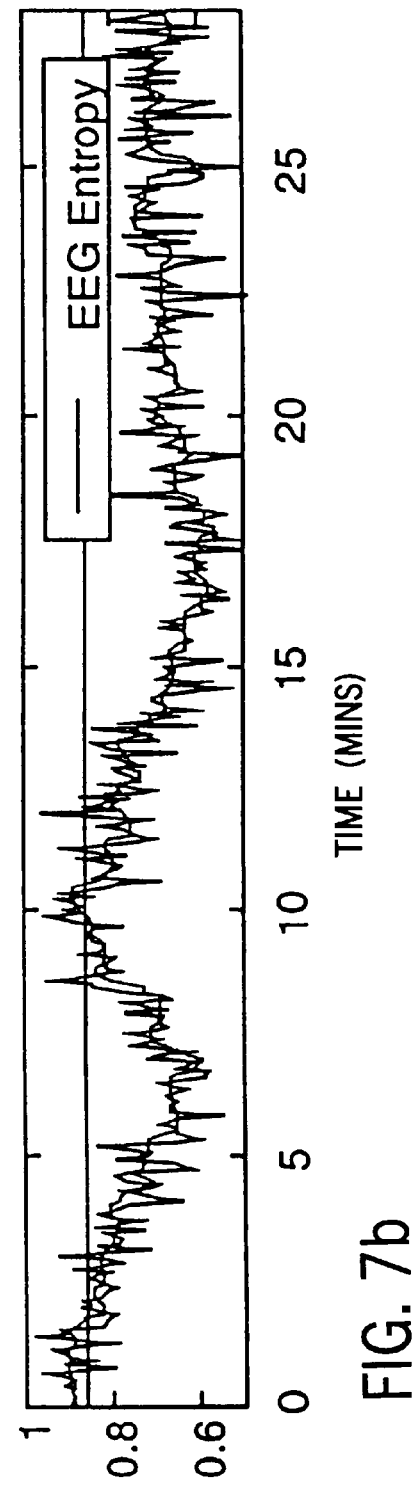
Figure 7C:
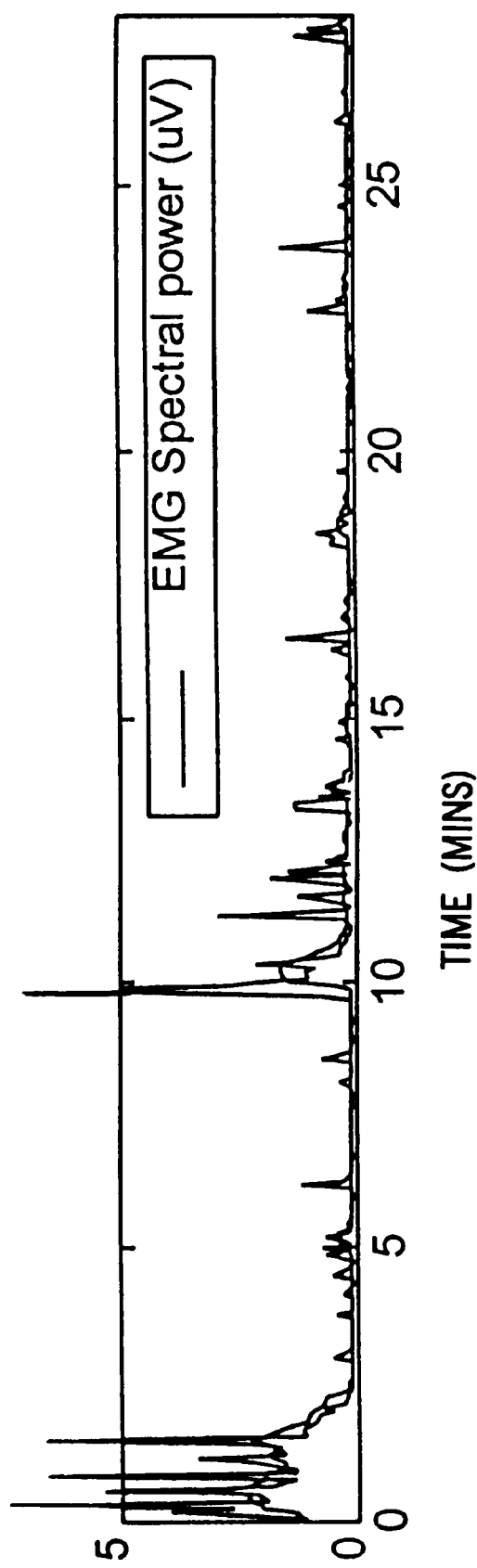

The components of the diagnostic indicator or index described above are shown in FIG. 7. An anesthetic agent is administered as a bolus at time zero. The patient enters unconsciousness, as shown by an OAAS level below line 10 in FIG. 7a, thereafter emerges for a short period of time, responsive to stimulation or the lack of further anesthetic agents, and is thereafter rendered unconscious. FIG. 7b shows the entropy indication as obtained from steps 120 and 122 of FIG. 6. FIG. 7c shows the EMG amplitude obtained from steps 126 and 128 as a root-mean-squared sum over the EMG range of the Fourier spectrum. Data for five seconds are shown as the jagged lines. The smoother lines indicate one minute median filtered values.

The graph of entropy as it relates to the hypnotic state of the patent resembles that of FIGS. 2 and 4. With respect to the EMG activity, during the first two minutes following time zero, there is considerable EMG activity indicating that the frontal muscle of the patient is active. Thereafter, the EMG activity decreases together with the patient becoming unconscious. At the ten minute point, the unequivocal and immediate indication of abrupt frontalis muscle reactivation given by the EMG amplitude is clearly apparent from FIG. 7c and will be reflected in the diagnostic indicator provided in step 128. This will advise the anesthesiologist that the patient is emerging from the anesthesia at that time.

Figure 8:
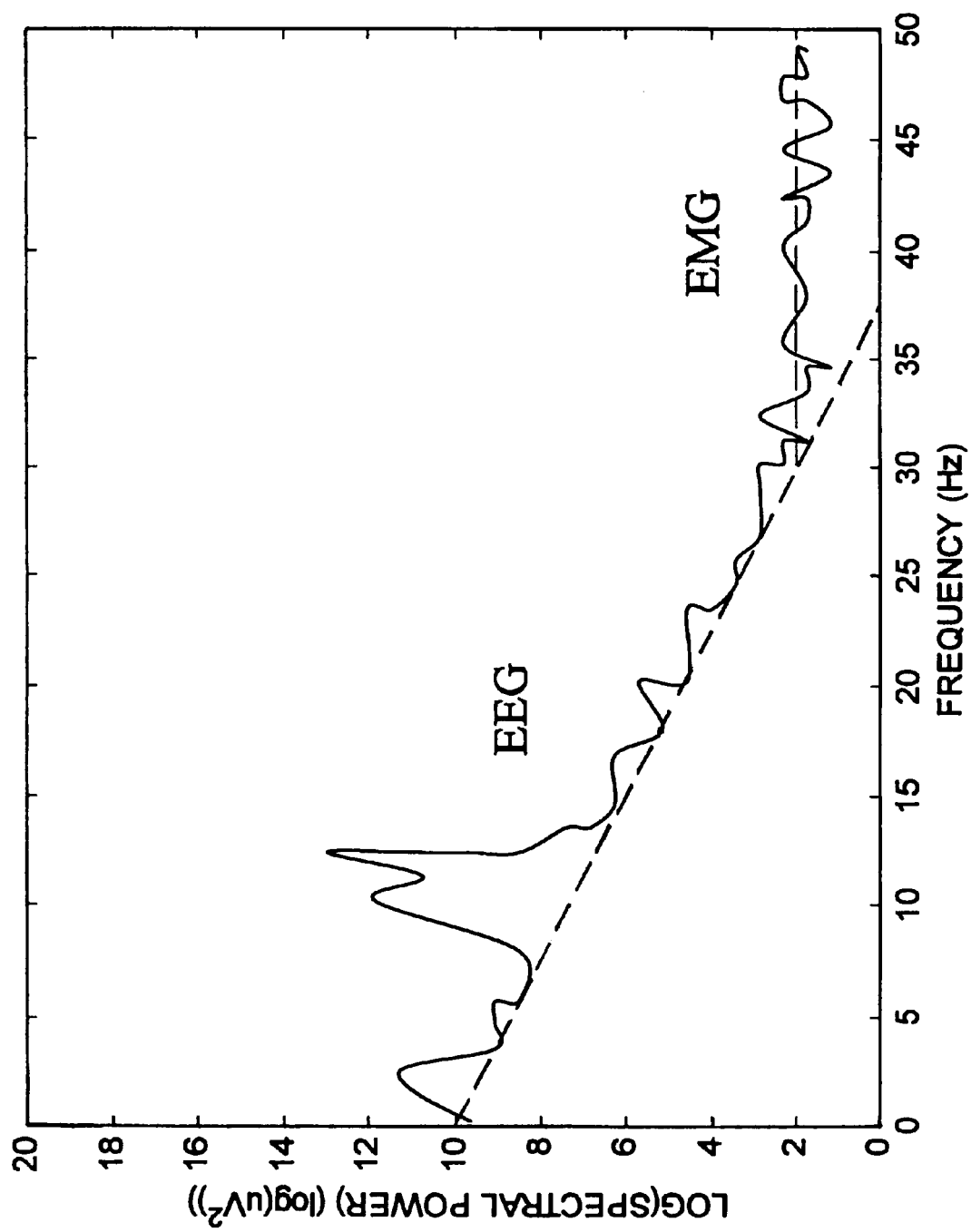
FIG. 8 is a graph showing EEG and EMG signal properties over a range of frequencies.

In another embodiment of the invention, incorporation of EMG signal data into a diagnostic indicator or index can be obtained by widening the frequency range of entropy or irregularity computations to one which extends from the EEG range into the EMG range thereby to include both EEG and EMG signal data. While EEG power decreases exponentially fast at high frequencies, EMG power is much less frequency-dependent and the corresponding EMG spectrum extends over a wide frequency range to above 100 Hz. This can be seen from FIG. 8 that shows the logarithm of spectral power over a range of frequencies with a general indication of the presence of EEG and EMG signal data. There exists no clear frequency boundary for the EEG and EMG data signals and an intermediate frequency range between 30 Hz and 50 Hz contains both EEG and EMG components overlapping each other.

In providing an entropy based indicator obtained from a frequency range containing both EEG and EMG spectra, it is to be appreciated that this represents a departure from the customary expression of, particularly, EMG signal data. That is, as noted above in connection with the first embodiment of the present invention, EMG signal characteristics are customarily expressed as a voltage amplitude, for example as a root mean squared spectral amplitude, and the amplitude of the voltage will vary as a result of variations in the EMG signal data. By contrast, EEG entropy is a dimensionless quantity which describes the amount of irregularity in the signal. When viewed from the entropic standpoint, the effect of EMG activity on the EEG signal is to create high frequency noise which increases the entropy of the combined signal. Entropy varies from 0 to 1, and the values are independent of the amplitude of the signal. The entropic expression of EEG signal data and the amplitude expression of the EMG signal data thus present a formal incompatibility which is overcome in the present invention by the use of entropy as a characteristics of both signal data.

Further, this embodiment of the invention represents a departure from the previous entropic treatment of EEG signal data which has been limited to the frequency range in which EEG predominates as compared with EMG. These frequency ranges are, for example, frequencies of 25 Hz and below (see Rezek et al.) or 32 Hz or below (see Bruhn et al.). See also FIG. 8. The present invention contemplates the use of frequencies in a range extending from some lower frequency, for example 0.5 Hz, to a higher frequency which is in excess of 32 Hz.

The second embodiment of the invention is explained using a frequency range of 0.5 Hz to about 150 Hz. It is deemed preferable to divide the extended frequency range into three-bands: a 0.5–47 Hz band; a 63–97 Hz band; and a 123–147 Hz band. The range is divided into the three bands at these frequencies in order to avoid the power line harmonics at 50/100 Hz or 60/120 Hz depending on the frequency of the alternating current power mains. The lowest band contains most of the EEG components, while the two upper bands include primarily EMG activity.

FIG. 9 is a flow chart showing, in general fashion, the steps of producing an improved diagnostic indication or index using a widened frequency range for the computation of spectral entropy in accordance with the second embodiment of the present invention. In step 200, the signal data corresponding to the biopotential signals appearing in the electrodes placed on the scalp of the patient is obtained. In step 210, the signal data is subjected to spectral decomposition, as by using Fourier transformation. As noted above, the spectral decomposition may be carried over a frequency range encompassing both the EEG signal data and the EMG signal data, for example, approximately 0.5 Hz to approximately 150 Hz. Also as noted above, the data is divided in spectral bands in order to omit frequencies at those of the power mains At step 212, the lower frequency band of the EEG-EMG spectral range as well as the higher frequency bands are processed together to compute a measure, such as spectral entropy, indicative of the complexity or irregularity of the combined EEG and EMG signal data and state of activity of the brain and the frontal muscles. This complexity value provides a combined indicator at step 214. As described above in connection with FIG. 6, because the EMG signal data is available for complete updating more frequently than the EEG signal data, updating the combined indicator at the repetition rate by which the EMG signal data parameter can be updated provides a rapid indication to the anesthesiologist of changes in the state of the patient.

Variations of the signal amplitude due to variations in the electrode contact properties etc. affect the EEG and EMG signal data in the same proportion to each other, so the combined EEG-EMG entropy indicator is not affected by the signal amplitude.

A parameter containing only EEG entropic data from a lower frequency band, say, 0.5 Hz to 32 Hz, may be used as a separate indicator as shown in steps 216 and 218. This can be used in connection with the EEG-EMG entropic indication to allow the anesthesiologist to determine what portion of the EEG-EMG entropic indicator comes from the EEG-dominant frequency range and what portion comes from the EMG-dominant range.

In the foregoing description, the concepts "EEG-EMG entropy" and "EEG-entropy" have been defined in terms of the particular frequency ranges chosen for the computations. In certain rare cases, which may occur when patient data is obtained from very elderly patients, the EEG signal may be particularly low. In such a case, the EMG-dominant range may extend to frequencies somewhat lower than 32 Hz, so that the "EEG-entropy" will contain a contribution from the EMG signal. Also in this case, however, the presence or absence of an EMG contribution can be readily deduced from a nonzero or zero difference between "EEG-EMG entropy" and "EEG-entropy." An alternative way of treating the frequency ranges that would avoid the above-mentioned problem with extremely low EEG signal would involve adaptive variation of the upper limit for the EEG range. That is, the EEG upper limit, described above as 30/32 Hz, would be altered in accordance with the magnitude of the EEG signal. This choice, however, could make the measurement less transparent and consistent, more "black-box-like" and therefore more difficult to be interpreted by the clinician.

A parameter containing the EMG entropic data from the higher frequency bands may be used as a separate parameter by computing the entropy at step 220 and providing the indicator at step 222. The various diagnostic indicators are collectively shown at step 224 in FIG. 8.

While the second embodiment of the invention has been explained using a wide frequency range, of, for example, 0.5 Hz to about 150 Hz, it has been found that through the use of only lower frequency portions of the range, for example the 0.5–47 Hz band described above, improved rejection of high frequency signal artifacts may be obtained.

Also, while the embodiments of the invention have been described above as utilizing Fourier transformation to decompose the spectrum of signals contained in the electrode biopotentials, other transformations, such as various wavelet transformations, may be employed. In order to obtain the corresponding indicators for pure EEG entropy, EEG-EMG entropy, and/or EMG entropy, the basis functions are divided into two classes, one including the basis functions for EEG activity, and the other including the basis functions for EMG activity. After this classification, the indices for pure EEG entropy and EEG-EMG entropy are computed as described above. It is plausible that for better separation of the EEG and EMG components, a set of basis functions including wavelets emulating the shapes of the EMG spikes may extract the EMG component more effectively.

FIG. 10 illustrates, as a function of time, the behavior of a pure EEG entropy parameter and the combined EEG-EMG entropy parameter along with the depth of anesthesia, as evaluated by an anesthesiologist on an OAAS scale. Also shown is EMG signal data as conventionally expressed as root mean squared spectral amplitude. The jagged lines show values computed from 5 seconds of data, while the smoother lines show one-minute median filtered values. In this Figure, all frequency components are calculated using time windows of similar lengths. An anesthetic agent is administered as a bolus at time zero.

During the first two minutes, during which time the patient is awake, the EEG entropy is high indicating that the patient is conscious. Also, there is a lot of EMG activity present as can be seen from the graph of FIG. 10d showing EMG amplitude. As a result of the high EMG activity, the combined EEG-EMG entropy shown in FIG. 10b also shows relatively high values.

Figure 10A:
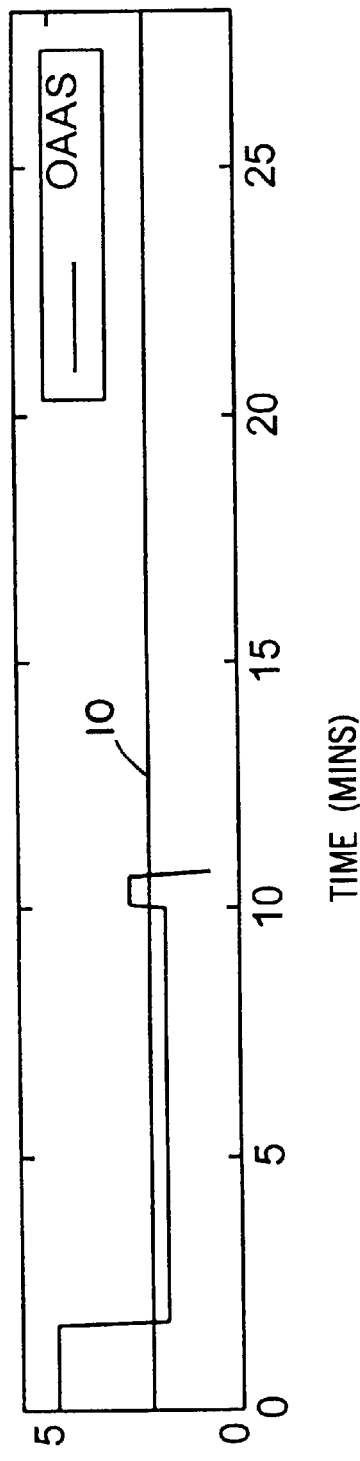
FIGS. 10a, 10b, 10c, and 10d are graphs showing OAAS levels and corresponding EEG and EMG based indicators of the depth of anesthesia.

At about the two minute point the patient loses consciousness as shown in FIG. 10a when the OAAS score falls below line 10. The EEG-EMG entropy indicator and the EEG entropy indicator, produced at steps 218 and 226, respectively, of FIG. 9 follow each other down below line 40 demarcating the transition to unconsciousness indicating deepening hypnosis. See FIGS. 10b and 10c. Simultaneously, the EMG activity largely disappears as shown in FIG. 10d.

Figure 10B:
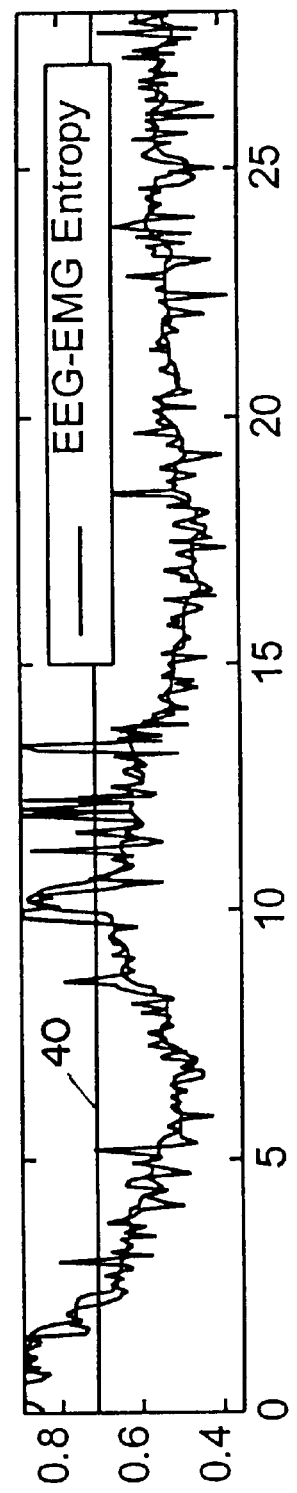
Figure 10C:
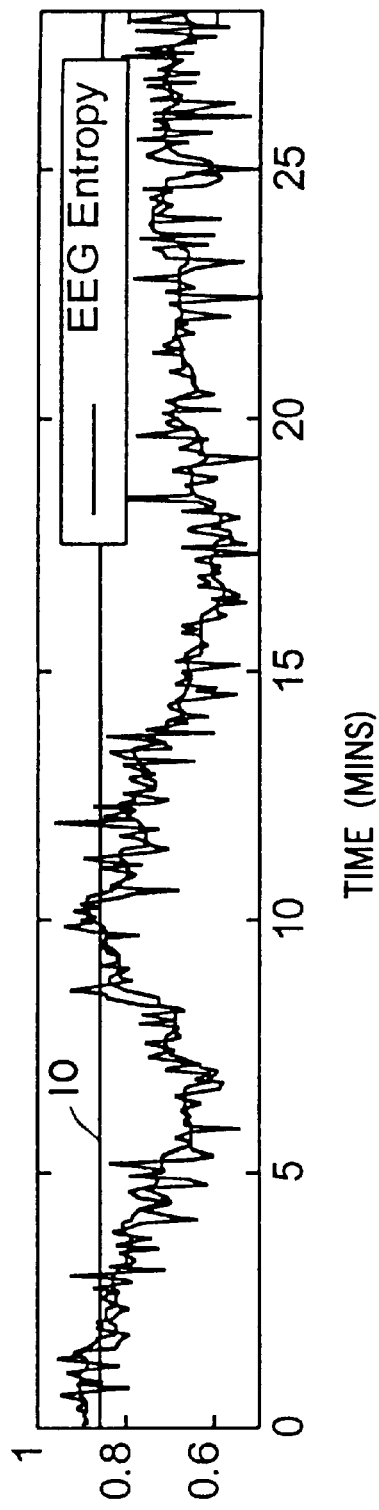
Figure 10D:
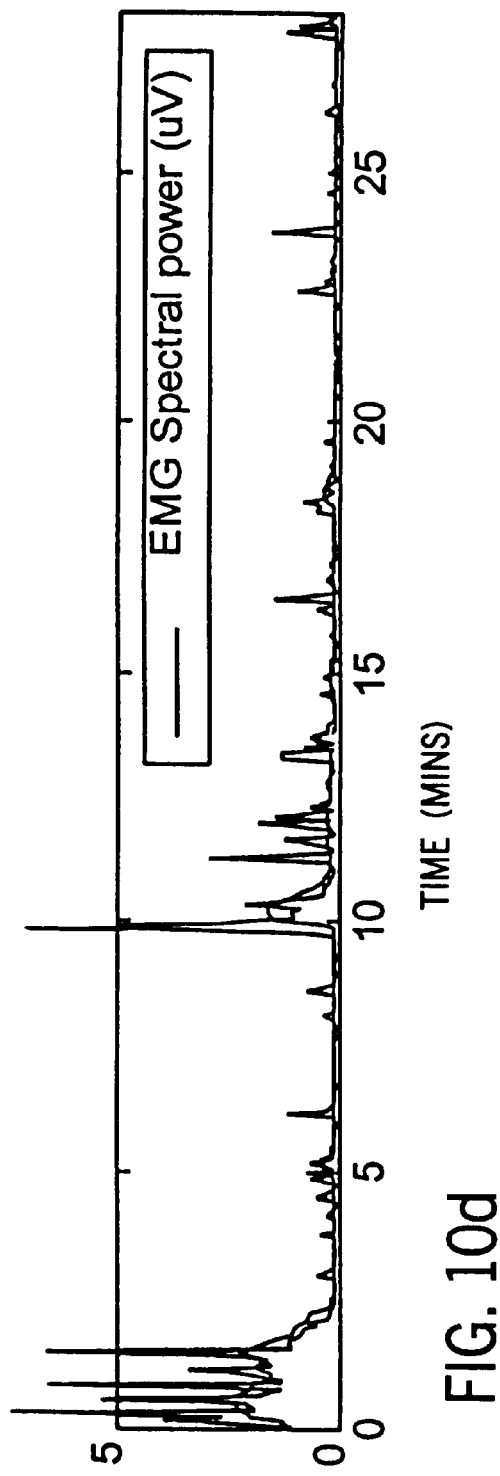

At about 6–7 minutes both the entropy values of FIGS. 10b and 10c show that anesthesia starts to lighten. This is because no further hypnotics have been administered. At about ten minutes, the patient wakes up and significant EMG activity again emerges. The pure EEG entropy indicator show in FIG. 10c predicts and indicates the recovery, and the EMG effect in the combined EEG-EMG entropy indictor shown in FIG. 10b makes this more apparent.

Thereafter following the ten minute point, patient is subsequently anesthetized again. The EMG activity gradually disappears as shown in FIG. 10d and EMG-EEG entropy indicator reduces to a pure EEG entropy indicator, as can be seen by a comparison of FIGS. 10b and 10c.

In both curves EEG-EMG-Entropy and EEG-Entropy, the values computed from 5 seconds of data have a large variance. This is due to the low frequencies present in both quantities, for which the 5 second time window is too short.

It is advantageous to scale the EEG-entropy parameter obtained in step 2186 of FIG. 9 and the EEG-EMG entropy parameter obtained in step 214 in such a way that they coincide exactly when the EMG activity ceases completely, as this scaling allows for simultaneous graphical representation of the two pieces of information. This can be done in the following way. Take the frequency range 0.5 to 32 Hz containing mainly EEG signal data to be frequency range $R_1$. Take the frequency range 32 to 147 Hz, with the power line frequencies removed, to be frequency range $R_2$ for mainly EMG signal data.

Perform for the frequency ranges $[R_1]=[EEG]$ and $[R_1]+[R2]=[EEG]+[EMG]$ the steps 1–3 of the Rezek algorithm (Eqs. (1)–(3)) to obtain $$S[R_1] = \sum_{R_1} P_n(f_i)\log\left(\frac{1}{P_n(f_i)}\right) \tag{5}$$

and $$S[R_1 + R_2] = \sum_{R_1+R_2} P_n(f_i)\log\left(\frac{1}{P_n(f_i)}\right) \tag{6}$$

As the frequencies in range $R_2$ are substantially higher then the frequencies in range $R_1$, in step 1 (Eq. (1)) a shorter time window is sufficient for computation of the Fourier components in the frequency range $R_2$ than for frequency range $R_1$. For example, the window length for frequency range $R_1$ could be equal to 1 minute, and the window length for the frequency range $R_2$ equal to 5 seconds.

Assume for a moment that $P_n(f_i)=0$ for all $f_i$ within the range $[R_2]$. In this case, the normalization constant $C_n[R_1+R_2]=C_n[R_1]$ and, consequently, the normalized spectra $P_n[R_1+R_2]$ and $P_n[R_1]$ (step 2) are equal. It follows that the unnormalized spectral entropies give by Eqs. (5) and (6) are equal. If these entropy values are now normalized according to Eq. (4), they will no longer be equal, because the normalization factor $\log(N[R_1+R_2])$ is obviously larger than $\log(N[R_1])$. This situation can be corrected by redefining the normalized entropy $S_N[R_1]$ in the following way:

$$S_N[R_1] = \frac{\log(N[R_1])}{\log(N[R_1+R_2])}\frac{S[R_1]}{\log(N[R_1])} = \frac{S[R_1]}{\log(N[R_1+R_2])} \tag{7}$$

The normalized entropy $S_N[R_1+R_2]$ can be defined as previously stated in Eq. (4):

$$S_N[R_1 + R_2] = \frac{S[R_1 + R_2]}{\log(N[R_1+R_2])} \tag{8}$$

According to these definitions, the EEG-EMG entropy varies from 0 to 1, whereas the pure EEG entropy varies from 0 to $\log(N[R_1])/\log(N[R_1+R_2])<1$. The two entropy values coincide when there is no EMG activity so that $P(f_i)=0$ for all $f_i$ within the range $[R_2]$. When EMG activity is present, EEG-EMG entropy is larger than the pure EEG entropy.

In practice, a digital filter is commonly used in processing the signal data obtained from the patient's biopotentials. Due to the characteristics of such a filter the computed entropy of a completely random signal, i.e. white noise, is usually slightly less than 1. For this reason, the entropies may be multiplied by a constant value so as to maintain the above described normalization.

Figure 11:
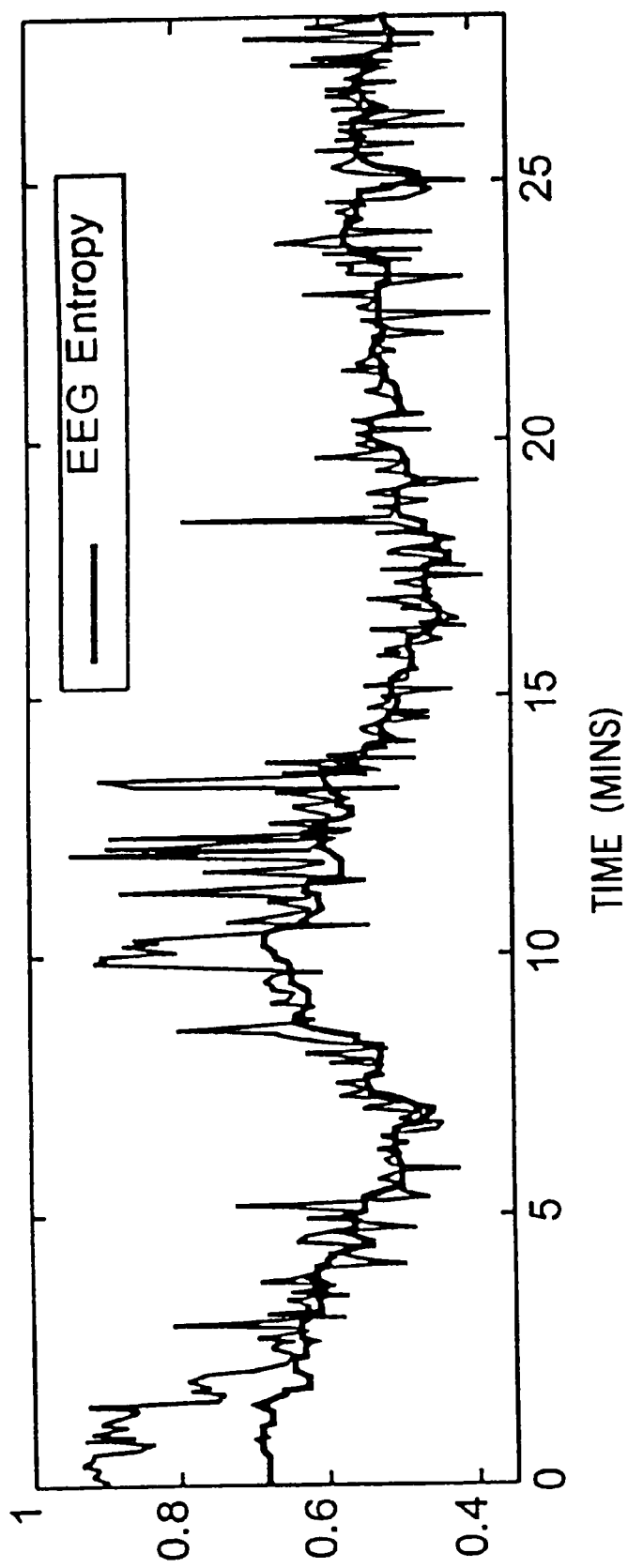
FIG. 11 is a graph showing combined EEG and EMG entropy values.

FIG. 11 shows one example of the resulting normalized EEG entropy $S_N[R_1]$ (thick curve) together with the normalized EEG-EMG entropy $S_N[R_1+R_2]$ (thin curve). It can be noticed that in the period from 7 to 10 minutes during which hypnosis is getting lighter, the EEG+EMG entropy increases faster than EEG entropy. When presented in this manner, the EEG entropy gives reliable information of the trend behavior of the patient's brain activity, while the EEG-EMG entropy responds rapidly to fast changes.

Instead of the EEG entropy indicator and the EEG-EMG entropy indicator shown in FIG. 10, it is possible to compute the corresponding entropy indicator for EMG activity alone as shown in FIG. 9, steps 220, 222, and to use this together with the pure EEG entropy indicator obtained in steps 216, 218. However, some care must be taken with respect to this approach. When EMG activity ceases due to relaxation of the muscles, some noise is left in the EMG range of the spectrum. The entropy of the noise may be relatively high and give a falsely high value for the level of EMG activity. Therefore, when EMG activity is considered separately and the concept of entropy is used for computations, a noise level should be established below which the EMG signal is considered to be zero. Thus, simply computing spectral power would be a more natural way to treat pure EMG data.

While the foregoing embodiment is described using two frequency ranges, $R_1$, $R_2$ of 0.5–32 Hz and 32–147 Hz, respectively, it will be appreciated that these ideas can be generalized to a case in which the number of frequency ranges is larger than two. In this generalization, a set of time windows of different lengths, corresponding to the chosen frequency ranges $R_1, R_2, \ldots R_M$, can be utilized. The length of each window can be optimized for the particular frequency range so that not more than the necessary amount of existing, historical data is used. The resulting entropy parameter $S_n[R_1+R_2+\ldots+R_M]$ will then have optimally fast response time.

Figure 12:
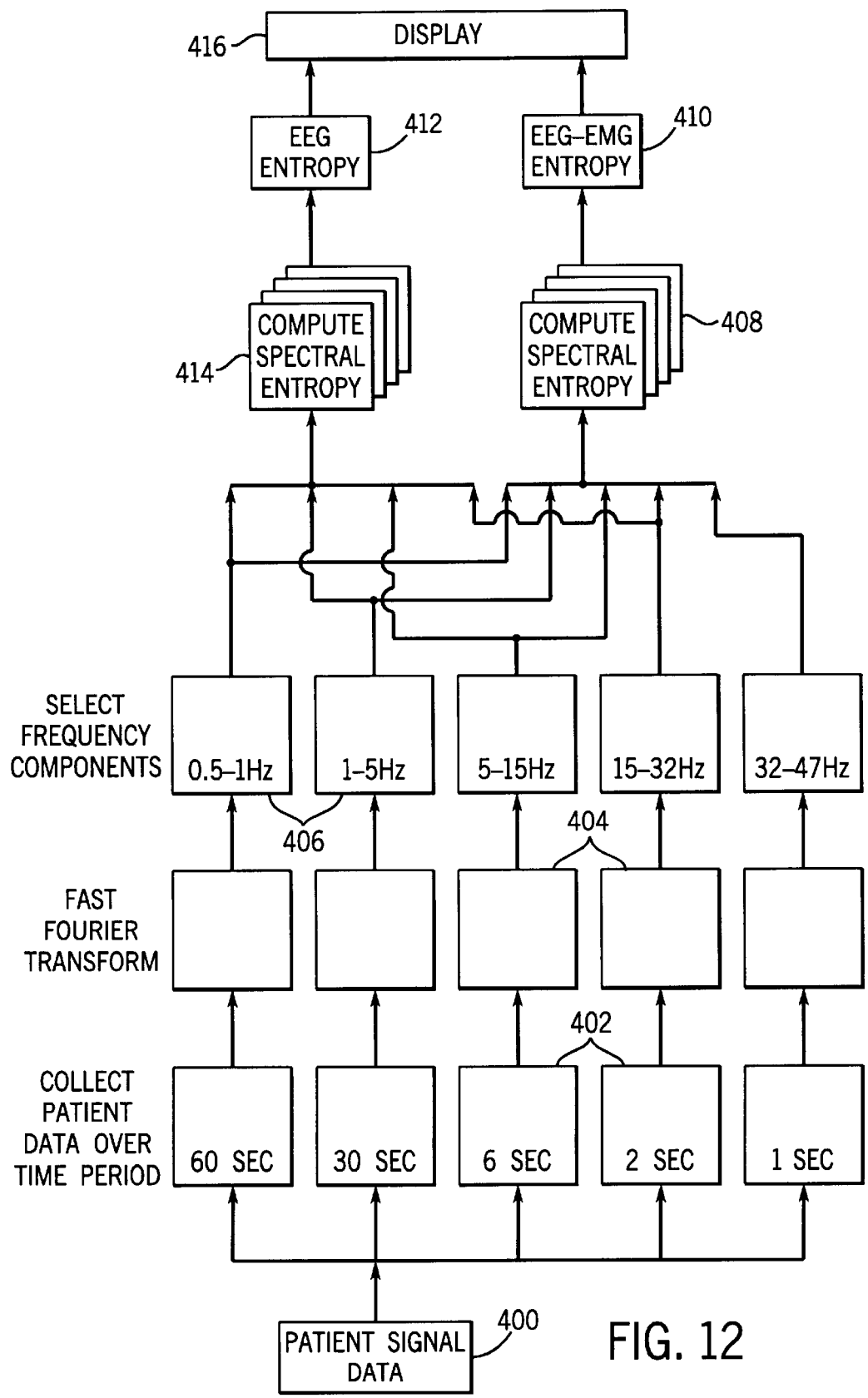
FIG. 12 is a flow chart showing a further embodiment of the present invention.

FIG. 12 shows such a further embodiment of the present invention using the frequency band of 0.5–47 Hz as a non-limiting example. Patient signal data is obtained at step 400. The patient data is collected over a plurality of periods, or time windows, of selected lengths in step 402. In the explanatory embodiment of the invention shown in FIG. 12, five time windows are utilized having lengths of 1 second, 2 seconds, 6 seconds, 30 seconds, and 60 seconds. The patient data of each of the time windows are subjected to a fast Fourier transform (FFT) or other suitable technique at step 404 to decompose the patient data into spectrums of component frequencies. Appropriate frequency components are then selected from the spectrum of each of the time windows in step 406 for use in determining a complexity or irregularity measure, such as spectral entropy. In this example, the selection has been carried out in such a way that at least 30 cycles have been included for the evaluation of each frequency component.

| Time Window | Frequency Range |
| --- | --- |
| 1 second | 32 to 47 Hz |
| 2 seconds | 15 to 32 Hz |
| 6 seconds | 5 to 15 Hz |
| 30 seconds | 1 to 5 Hz |
| 60 seconds | 0.5 to 1 Hz |

The selected frequency components from all time windows are then used in step 408 to compute a complexity measure, for example spectral entropy, as in the manner described by Rezek et al. This provides a spectral entropy 410 for all of the 0.5 to 47 Hz frequency range of the patient data signal. The result is a combined EEG-EMG spectral entropy.

Lower frequency components from longer time windows containing large amounts of EEG signal are further used to compute an EEG complexity measure, such as spectral entropy, 412 in step 414. FIG. 12 shows use of frequency components extending over 0.5 to 32 Hz range for this purpose.

Figure 13:
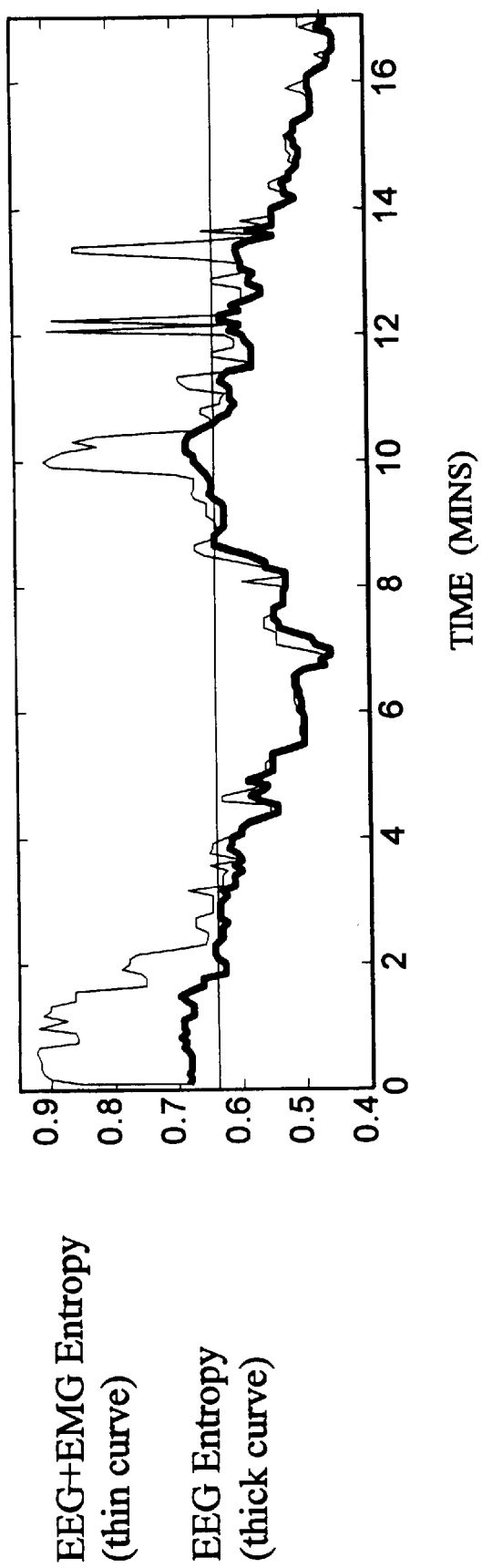
FIG. 13 is a graph showing combined EEG and EMG entropy values and EEG entropy values for the embodiment of the invention of FIG. 11.

The resulting spectral entropies obtained in steps 308 and 310 may be provided to a display in step 416 for use for diagnostic or other purposes. FIG. 13 shows such a display with appropriate scaling, as described above.

The determination of the spectral entropies may be carried out at a repetition rate governed by the length of the shortest time window. In the example shown in FIG. 12, this would be every one second. The signal data used for the Fourier transform for time windows longer than the shortest time window would include one second of new signal data and a remaining portion of existing data. As noted above, the lengths of the time windows can be optimized for the particular frequency ranges so that not more than the necessary amount of existing data is utilized. The resulting entropy parameters will then have optimally fast response time.

Figure 14:
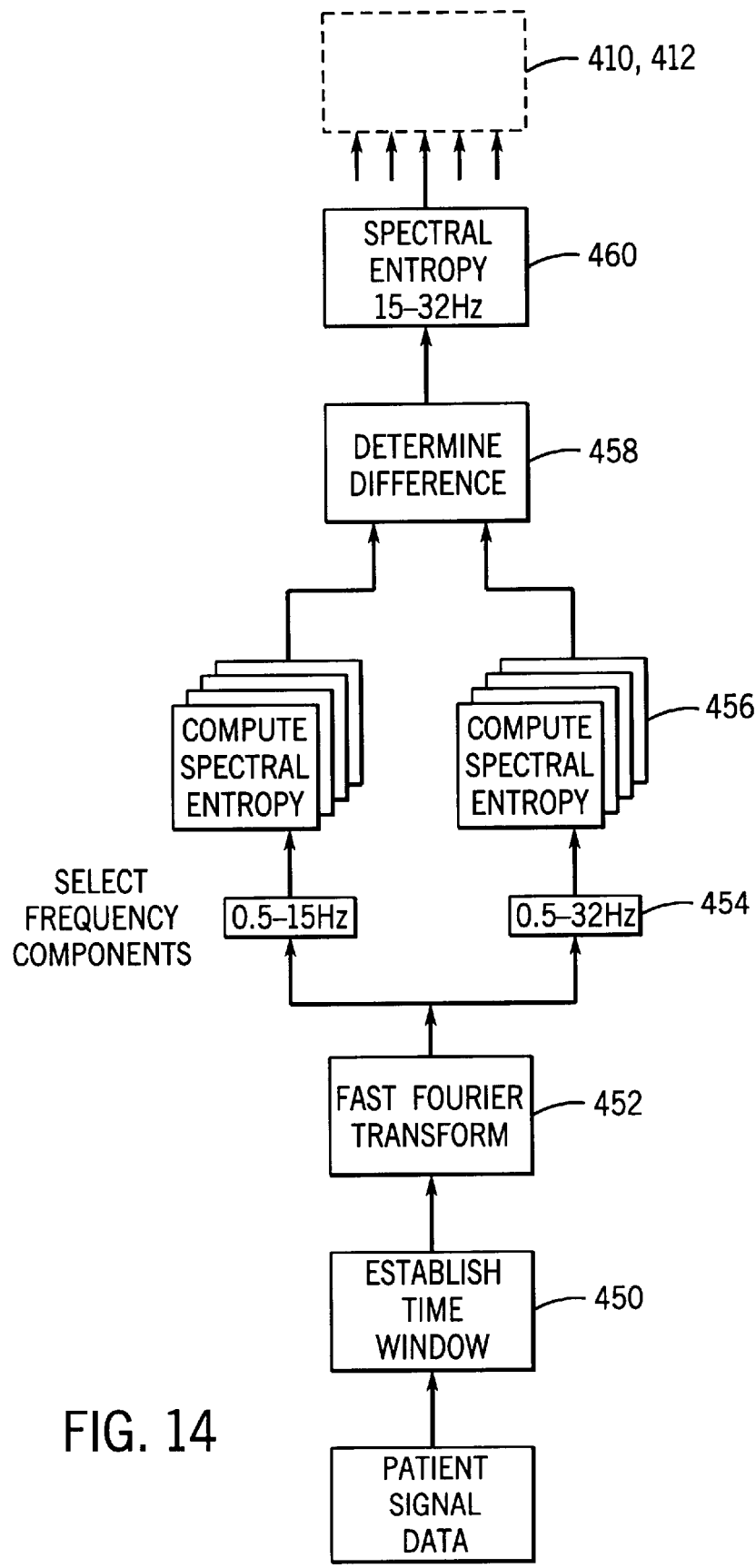
FIG. 14 is a partial flow chart of a modification of the embodiment of the invention shown in FIG. 12.

It should be noted that it is also possible to structure the computations of spectral entropy differently from that shown in FIG. 12 so that the steps of dividing the signal in time windows of different lengths, selecting particular frequency ranges, and computing spectral entropies are performed in a different order. Thus, one may compute spectral entropies from the same time window for two different frequency ranges, for example for 0.5–15 Hz and 0.5–32 Hz, and use the difference of these two entropy values as the entropy contribution of the frequency range from 15 Hz to 32 Hz from this particular time window. This is shown in FIG. 14 in which a time window is established at step 450 for collecting the patient signal data. A fast Fourier transform or other spectral decomposition is carried out in step 452 to extract the frequency components of the patient signal data. Thereafter the frequency ranges for the frequency components, such as 0.5 to 15 Hz and 0.5 to 32 Hz are selected at step 454 and the spectral entropies, or other complexity or irregularity measures, computed for each of these frequency ranges at step 456. Thereafter the difference between the two spectral entropies is determined at step 458 and provided to the spectral entropy indication 410 as the entropy contribution 460 from the differential frequency range, i.e. 15 to 32 Hz in the example used herein. Corresponding steps would be carried out for other frequency ranges used to establish the desired spectral entropy indicator 410 and 412.

Figure 15:
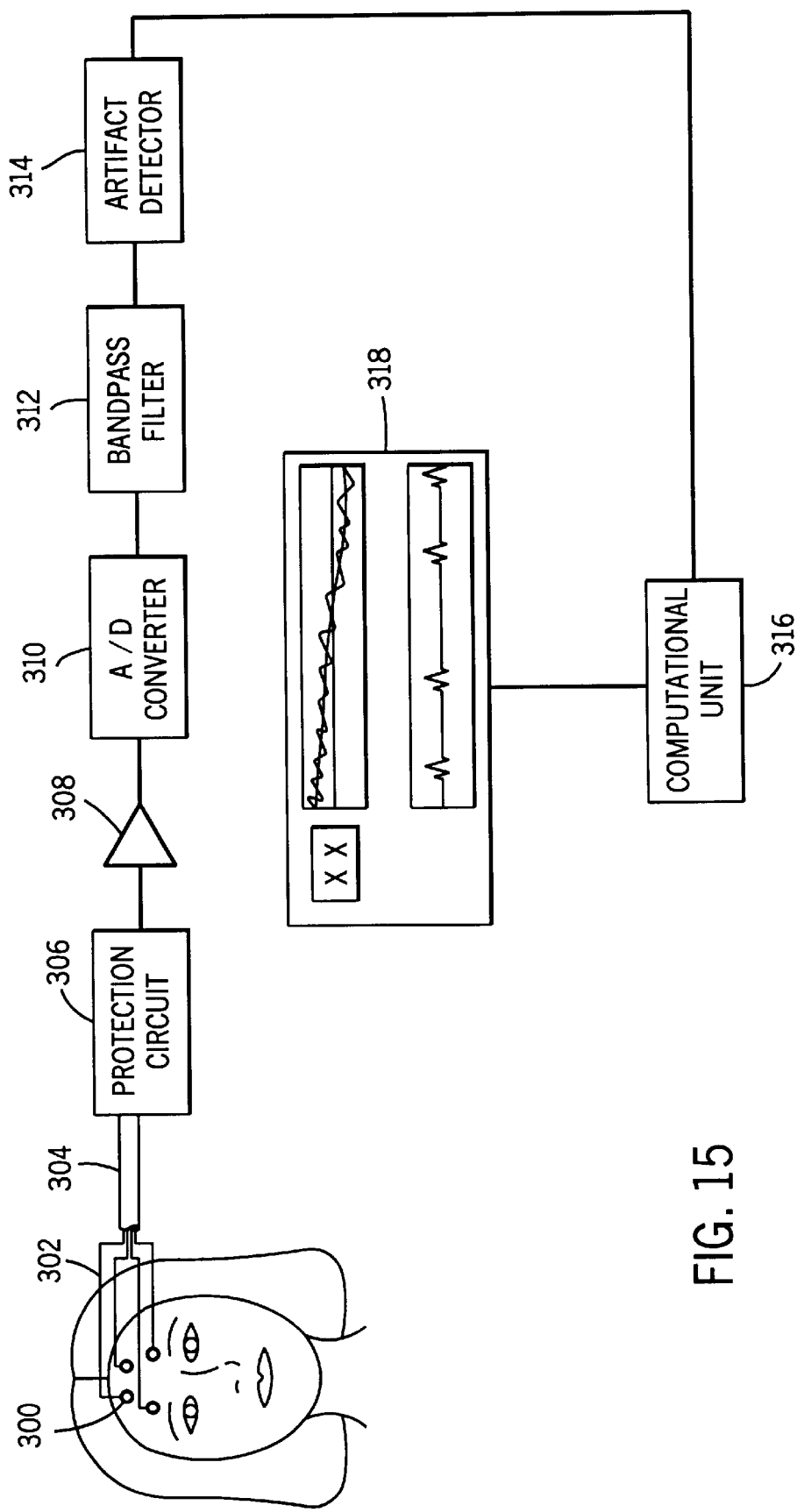
FIG. 15 shows apparatus for carrying out the present invention.

Apparatus for carrying out the present invention is shown in FIG. 15. Electrodes 300 are applied to the head of the patient in a desired manner. Preferably, at least some of the electrodes are applied to the forehead of the patient. At least one pair and usually a plurality of pairs of electrodes are utilized. The biopotentials appearing in the electrodes are received in conductors 302 and are collected into patient cable 304.

Cable 304 connects conductors 302 to protection circuit 306 which is operative in the event the patient is subjected to electro-surgery or cardiac defibrillation. Electro-surgery employs alternating current at radio frequencies to cut tissue and cauterize bleeding blood vessels. A defibrillator delivers a short current pulse to arrest arrhythmia in the heart muscle. Protection circuit 306 can be eliminated if the design of the subsequent circuitry can tolerate these interferences without signal rejection.

The output of protection circuit 306 is amplified by amplifier 308 and subjected to analog to digital conversion in analog/digital converter 310. Thereafter the signals are provided to bandpass filter at filter 312 that removes noise and line frequency harmonics from the signals. The output from bandpass filter 312 is connected to artifact detector 314.

Artifact detector 314 detects artifacts arising from electrocardiac activity, and other sources. The output of artifact detector 314 is connected to computational unit 316 which carries out the steps of the methods described above and shown in FIGS. 6, 9, and 12 and produces an output of the type shown in FIGS. 3, 4, 5, 7, 10, 11, and 13 in display 318. Or, the information may be presented in display 318 in numerical form. Display 318 may also display other physiological data, such as electrocardiographic data, breath rate, pulse, blood pressure, etc., obtained from other measurement units. While artifact detector 314 is used to remove artifacts, the presence of artifacts can also be dealt with in the signal processing occurring in computational unit 316.

The invention has been described above in connection with cerebral states induced by the administration of an anesthetic agent. However, it will be appreciated that the method and apparatus may be used in connection with other physiological conditions which are reflected in EEG and EMG signal data obtained from a patient and with drugs other than anesthetic agents. It is therefore recognized that other equivalents, alternatives, and modifications aside from those expressly stated, are possible and within the scope of the appended claims.

What is claimed is:

1. A method for ascertaining the cerebral state of a patient, including a state resulting from the administration of a drug, said method comprising the steps of:
   (a) obtaining biopotential signal data from the patient, the biopotential signal data containing EEG signal data and EMG signal data, the EMG signal data being primarily of a higher frequency than the EEG signal data which is primarily of a lower frequency;
   (b) collecting the biopotential signal data over a plurality of time periods of differing lengths;
   (c) subjecting the biopotential signal data of each of the time periods to spectral decomposition to obtain the frequency components of the collected biopotential signal data;
   (d) selecting frequency components in a selected frequency band from the decomposed biopotential signal data for each of the time periods;
   (e) analyzing the frequency components of a desired number of the frequency bands to obtain a measure of the complexity of the frequency components over a frequency range formed from the selected frequency bands; and
   (f) providing the measure so obtained as an indication of the cerebral state of the patient.

2. The method according to claim 1 further defined as establishing the lengths of the time periods dependent on the frequency band of the frequency components selected in step (d).

3. The method according to claim 2 further defined as establishing the lengths of the time periods to provide a desired minimum number of cycles of biopotential signal data frequency components in the frequency band selected in step (d).

4. The method according to claim 1 further including the step of establishing the lengths of the time periods to produce optimally fast response time in ascertaining the cerebral state of the patient.

5. The method according to claim 1 further defined as utilizing the frequency components of at least two frequency bands.

6. The method according to claim 5 further defined as establishing the frequency bands in accordance with the magnitude of at least one of the EEG and EMG signal data.

7. The method according to claim 1 wherein the frequency bands are selected to include at least one frequency band containing primarily EMG signal data.

8. The method according to claim 5 wherein the frequency bands are selected to include at least one frequency band containing primarily EEG signal data.

9. The method according to claim 8 wherein the frequency bands are selected to include a plurality of frequency bands containing primarily EEG signal data.

10. The method according to claim 1 wherein step (e) is further defined as analyzing frequency components for frequency bands including EEG and EMG signal data.

11. The method according to claim 10 further including the steps of additionally analyzing frequency components for a frequency band or frequency bands including primarily EEG signal data to obtain a measure of the complexity of the frequency components and providing the complexity measure so obtained as a further indication of the cerebral state of the patient.

12. The method according to claim 1 wherein step (d) is further defined as selecting frequency components in two desired frequency bands for the biopotential signal data for at least one of the time periods; step (e) is further defined as analyzing the frequency components in the two frequency bands to obtain the complexity measure; and the method includes the step of determining the difference between the two complexity measures and providing the difference for use in the indication of the cerebral state of the patient.

13. The method according to claim 1 further defined as one for ascertaining the hypnotic state of the patient.

14. The method according to claim 1 wherein step (e) is further defined as obtaining a measure of the entropy of the frequency components as the indication.

15. The method according to claim 14 wherein step (e) is further defined as obtaining the spectral entropy of the frequency components as the indication.

16. The method according to claim 14 wherein step (e) is further defined as obtaining the approximate entropy of the frequency components as the indication.

17. The method according to claim 1 wherein step (e) is further defined as obtaining a Lempel-Ziv complexity measure of the frequency components as the indication.

18. A method according to claim 1 wherein step (e) is further defined as obtaining the measure of complexity from fractal spectrum analysis.

19. The method according to claim 1 further defined as carrying out the spectral decomposition by means of a Fourier transform.

20. The method according to claim 1 further defined as repeating steps (e) and (f) to update the indication.

21. The method according to claim 20 further defined as one for ascertaining the hypnotic state of a patient.

22. A method for ascertaining the cerebral state of a patient, including a state resulting from the administration of a drug, said method comprising the steps of:
   (a) obtaining biopotential signal data from the patient, the biopotential signal data containing EEG signal data and EMG signal data, the EMG signal data being primarily of a higher frequency than the EEG signal data which is primarily of a lower frequency;
   (b) collecting the biopotential signal data over a plurality of time periods of differing lengths;
   (c) subjecting the biopotential signal data of each of the time periods to decomposition to a set of basis functions;
   (d) selecting spectral components in a desired class of basis functions for each of the time periods;
   (e) analyzing the spectral components of a desired number of the classes of basis functions to obtain a complexity measure of the spectral components from the desired number of classes of basis functions; and
   (f) providing the measure so obtained as an indication of the cerebral state of the patient.

23. The method according to claim 22 wherein step (d) is further defined as selecting spectral components in two desired classes of basis function for the biopotential signal data for at least one of the time periods; step (e) is further defined as analyzing the spectral components in the two classes to obtain the complexity measures; and the method includes the step of determining the difference between the two complexity measures and providing the difference for use in the indication of the cerebral state of the patient.

24. Apparatus for ascertaining the cerebral state of a patient, including a state resulting from the administration of a drug, said apparatus comprising:
   (a) means for obtaining biopotential signal data from the patient, the biopotential signal data containing EEG signal data and EMG signal data, the EMG signal data being primarily of a higher frequency than the EEG signal data which is primarily of a lower frequency;
   (b) means for recording the biopotential signal data over a plurality of time periods of differing lengths;
   (c) means for spectrally decomposing the biopotential signal data of each of the time periods to obtain the frequency components of the collected biopotential signal data;
   (d) means for selecting frequency components in a selected frequency band from the decomposed biopotential signal data for each of the time periods;
   (e) means analyzing the frequency components of a desired number of the frequency bands to obtain a measure of the complexity of the frequency components over a frequency range formed from the selected frequency bands; and
   (f) means providing the measure so obtained as an indication of the cerebral state of the patient.

25. The apparatus according to claim 24 wherein said recording means is further defined as establishing the lengths of the time periods dependent on the frequency band of the selected frequency components.

26. The apparatus according to claim 24 wherein said analyzing means is further defined as utilizing the frequency components of at least two frequency bands.

27. The apparatus according to claim 24 wherein said selecting means selects frequency bands including at least one frequency and containing primarily EMG signal data.

28. The apparatus according to claim 24 wherein said selecting means selects frequency bands including at least one frequency and containing primarily EEG signal data.

29. The apparatus according to claim 28 wherein said selecting means selects frequency bands including a plurality of frequency bands containing primarily EEG signal data.

30. The apparatus according to claim 24 further including means or additionally analyzing frequency components for a frequency band or frequency bands including primarily EEG signal data to obtain a measure of the complexity of the frequency components and means providing the complexity measure so obtained as a further indication of the cerebral state of the patient.

31. The apparatus according to claim 24 further including means for selecting frequency components in two desired frequency bands for the biopotential signal data for at least one of the time periods; said analyzing means further analyzes the frequency components in the two frequency bands to obtain the complexity measure; said apparatus includes means for determining the difference between the two complexity measures and said providing means provides the difference for use in the indication of the cerebral state of the patient.

32. The apparatus according to claim 24 further defined as one for ascertaining the hypnotic state of the patient.

33. The apparatus according to claim 24 wherein said analyzing means is further defined as obtaining a measure of the entropy of the frequency components as the indication.

34. The apparatus according to claim 33 wherein said analyzing means is further defined as obtaining the spectral entropy of the frequency components as the indication.

35. The apparatus according to claim 33 wherein said analyzing means is further defined as obtaining the approximate entropy of the frequency components as the indication.

36. The apparatus according to claim 24 wherein said analyzing means is further defined as obtaining a Lempel-Ziv complexity measure of the frequency components as the indication.

37. A apparatus according to claim 24 wherein said analyzing means is further defined as obtaining the measure of complexity from fractal spectrum analysis.

38. The apparatus according to claim 24 wherein said spectral decomposition means is further defined as carrying out the spectral decomposition by means of a Fourier transform.

39. Apparatus for ascertaining the cerebral state of a patient, including a state resulting from the administration of a drug, said apparatus comprising:
   (a) means for obtaining biopotential signal data from the patient, the biopotential signal data containing EEG signal data and EMG signal data, the EMG signal data being primarily of a higher frequency than the EEG signal data which is primarily of a lower frequency;
   (b) means for recording the biopotential signal data over a plurality of time periods of differing length;
   (c) means for subjecting the biopotential signal data of each of the time periods to decomposition to a set of basis functions;
   (d) means for selecting spectral components in a desired class of basis functions for each of the time periods;
   (e) means analyzing the spectral components of a desired number of the classes of basis functions to obtain a complexity measure of the spectral components from the desired number of classes of basis functions; and
   (f) means for providing the measure so obtained as an indication of the cerebral state of the patient.

40. The apparatus according to claim 39 including means for further selecting spectral components in two desired classes of basis functions for the biopotential signal data for at least one of the time periods; said analyzing means further analyzes the spectral components in the two classes to obtain the complexity measures; said apparatus includes means for determining the difference between the two complexity measures and said providing means provides the difference for use in the indication of the cerebral state of the patient.

* * * * *